(12) United States Patent
Kim et al.

(10) Patent No.: US 9,719,997 B2
(45) Date of Patent: Aug. 1, 2017

(54) METHODS OF LABELING CELLS WITH FLUOROQUINOLONE ANTIBIOTICS

(71) Applicant: POSTECH ACADEMY-INDUSTRY FOUNDATION, Gyeongsangbuk-do (KR)

(72) Inventors: Ki Hean Kim, Gyeongsangbuk-do (KR); Myoung Joon Kim, Seoul (KR); Jun Ho Lee, Seoul (KR); Seong Hun Lee, Daegu (KR); Jin Hyoung Park, Gangwon-do (KR); Bum Ju Kim, Gyeongsangbuk-do (KR); Tae Jun Wang, Busan (KR)

(73) Assignee: POSTECH ACADEMY-INDUSTRY FOUNDATION, Gyeongsangbuk-do (KR)

( * ) Notice: Subject to any disclaimer, the term of this patent is extended or adjusted under 35 U.S.C. 154(b) by 0 days.

(21) Appl. No.: 14/943,136

(22) Filed: Nov. 17, 2015

(65) Prior Publication Data

US 2016/0341734 A1 Nov. 24, 2016

(30) Foreign Application Priority Data

May 20, 2015 (KR) ........................ 10-2015-0070682

(51) Int. Cl.
*G01N 33/58* (2006.01)
*G01N 21/64* (2006.01)

(52) U.S. Cl.
CPC ....... *G01N 33/582* (2013.01); *G01N 21/6428* (2013.01); *G01N 2021/6439* (2013.01)

(58) Field of Classification Search
None
See application file for complete search history.

(56) References Cited

FOREIGN PATENT DOCUMENTS

GR 2005 100140 A * 11/2006

OTHER PUBLICATIONS

Zhang P. et al. Photochemical Properties and Reactions with Biomolecules of 4'-N-Acetyl Derivative of Norfloxacin. Zeitschrift fuer Physicalische Chemi 225(8)843-857, 2011.*
Lee S. et al. In vivo 3D Measurement of Moxifloxacin and Gatifloxacin Distributions in the Mouse Cornea Using Multiphoton Microscopy. Scientific Reports 6:25339, May 2016.*

* cited by examiner

*Primary Examiner* — Ralph Gitomer
(74) *Attorney, Agent, or Firm* — Occhiuti & Rohlicek LLP

(57) ABSTRACT

Provided are methods of labeling cells in at least one of a biological tissue, bacteria, and fungi with fluoroquinolone antibiotics (e.g., moxifloxacin and gatifloxacin).

4 Claims, 55 Drawing Sheets
(50 of 55 Drawing Sheet(s) Filed in Color)

$C_{21}H_{24}FN_3O_4 \cdot HCl$  Mol. Wt. 437.9

$C_{19}H_{22}FN_3O_4 \cdot 1.5H_2O$     Mol. Wt. 402.42

METHODS OF LABELING CELLS WITH FLUOROQUINOLONE ANTIBIOTICS

CROSS-REFERENCE TO RELATED APPLICATIONS

This application claims the benefit of priority of Korean Patent Application No. 10-2015-0070682 filed on May 20, 2015, all of which are incorporated by reference in their entirety herein.

BACKGROUND OF THE INVENTION

Field of the Invention

The present invention relates to a use of fluoroquinolone antibiotics.

Description of the Related Art

Labeling, fluorescence imaging, and measurement methods using fluorescent materials which are frequently used in biological researches are methods of fluorescently expressing only a predetermined area of interest in body organs of organisms except for humans and have an advantage of photographing with a high contrast ratio. However, currently, as a fluorescent label material targeted to a human body, only ICG and fluorescein are used for vascular labeling, but there are no materials used for labeling cells or microorganisms.

Fluoroquinolone antibiotics generally have single-photon fluorescence generating one fluorescent photon by one high-energy incident photon. However, since excited light expressing the fluoroquinolone antibiotics is in an ultraviolet-ray area in which moxifloxacin is 280 nm and gatifloxacin is 292 nm, the fluorescent characteristic is not used to determine bacteria causing diseases in cells in the human body and the like.

The material having the single-photon fluorescence may also have a multi-photon fluorescent characteristic which generates one fluorescent photon through cooperation of two or three low-energy incident photons such as two-photon fluorescence and three-photon fluorescence which are non-linear fluorescence. However, the multi-photon fluorescent characteristic may not be known until being actually experimentally verified, and fluorescence efficiency may be verified only by measuring.

Accordingly, currently, there are no fluorescent label materials used for the cells of the human body and the like, and in order to determine the bacterial, a method of diagnosing infectious bacteria is used.

The method of diagnosing the infectious bacteria is a method of verifying inflammation due to infection through a slit lamp, extracting a tissue at an inflammation portion by rubbing a cotton swab, and observing the extracted tissue through labeling or observing the extracted tissue after culture for several days. In the method, there is a disadvantage in that it takes a lot of time and thus a treatment time is delayed.

SUMMARY OF THE INVENTION

Therefore, an object of the present invention is to provide a use and a method of labeling cells in at least one of a biological tissue, bacteria, and fungi with fluoroquinolone antibiotics, a use of applying labeled cells in the body tissue to a method of diagnosing infectious bacteria by labeling the cells in the body tissue, and information on diagnosis of infectious bacteria and fungi.

An object of the present invention is achieved by labeling cells in at least one of a biological tissue, bacteria, and fungi in a use of fluoroquinolone antibiotics.

The tissue may include at least one of a cornea, a skin, and a bladder.

The labeling may use multi-photon fluorescence expression.

The fluoroquinolone antibiotics may include moxifloxacin.

The fluoroquinolone antibiotics may include gatifloxacin.

Another object of the present invention is achieved by labeling cells in a biological tissue to be used for a diagnosis method of at least of infectious bacteria and fungi in a use of fluoroquinolone antibiotics.

The tissue may include at least one of a cornea, a skin, and a bladder.

The infectious bacteria may include at least one of *pseudomonas, staphylococcus*, and the infectious fungi include at least one of the *aspergillus* and *candida*.

The labeling may use multi-photon fluorescence expression.

The fluoroquinolone antibiotics may include at least one of moxifloxacin and gatifloxacin.

Yet another object of the present invention is achieved by including preparing a tissue to be fluorescent-labeled by cell unit and administering the fluoroquinolone antibiotics to the tissue, in a labeling method of fluoroquinolone antibiotics.

The tissue may include at least one of a cornea, a skin, and a bladder.

The labeling may use multi-photon fluorescence expression.

The fluoroquinolone antibiotics may include at least one of moxifloxacin and gatifloxacin.

Still another object of the present invention is achieved by a method of providing information on at least one of infectious bacteria and fungi including: preparing a tissue to be fluorescent-labeled by cell unit; adding the fluoroquinolone antibiotics into the tissue and labeling the tissue; and providing information on infectious bacteria by inspecting the tissue through a multi-photon fluorescence-based optical image.

At least one of the infectious bacteria may include at least one of cornea, skin, and bladder bacteria.

The infectious bacteria may include at least one of *pseudomonas, staphylococcus*, and the infection fungi include at least one of *aspergillus* and *candida*.

The fluoroquinolone antibiotics may include at least one of moxifloxacin and gatifloxacin.

According to the present invention, it is possible to provide an object of the present invention is to provide a use and a method of labeling cells in at least one of a biological tissue, bacteria, and fungi with fluoroquinolone antibiotics, a use of applying labeled cells in at least one of the bacteria and fungi to a method of diagnosing infectious bacteria and fungi by labeling the cells in the biological tissue, and information on diagnosis of infectious bacteria and fungi.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A and 6A illustrate the corneal superficial epithelium, FIGS. 5B and 6B illustrate the corneal basal epithelium, FIGS. 5C and 6C illustrate the corneal stroma, FIGS. 5D and 6D illustrate the corneal endothelium.

DESCRIPTION OF EXEMPLARY EMBODIMENTS

Figure 1:
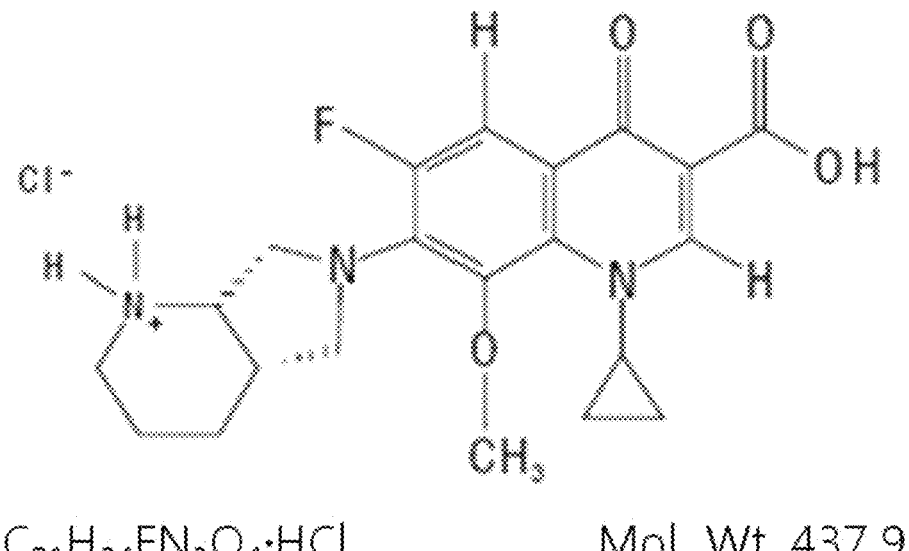
FIG. 1 illustrates a structural formula and a chemical formula of hydrochloride moxifloxacin used in the present invention.

The present invention provides a use of fluoroquinolone antibiotics labeling cells in a at least one of a biological tissue, bacteria, and fungi. and using the labeled cell in a diagnosis method of infectious bacteria and fungi.

In the present invention, the labeling method of cells in the at least one of a biological tissue, bacteria, and fungi. using the fluoroquinolone antibiotics includes (a) preparing a at least one of a biological tissue, bacteria, and fungi to be fluorescent-labeled by cell unit, and (b) adding fluoroquinolone antibiotics to at least one of the biological tissue, bacteria, and fungi.

Further, the present invention provides information on diagnosis of at least one of infectious bacteria and fungi. including (a) preparing a tissue to be fluorescent-labeled by cell unit, (b) adding and labeling fluoroquinolone antibiotics to the tissue, and (c) providing information on at least one of infectious bacteria and fungi by inspecting the tissue through a multi-photon fluorescent-based optical image.

A moving appearance of molecules, cells, and tissues of the organism may be observed through a fluorescence microscope when being treated by a fluorescent probe (FP). While electrons in the FP become in the excited state by the incident photon and return to the original site again, fluorescent photons having special colors are emitted.

When the fluorescent photons are emitted in the visible light area, it may be used to determine the bacteria causing the diseases in cells in the human body and the like. In the present invention, it was found that the fluoroquinolone antibiotics may be fluorescent-expressed in the visible light area as well as the ultraviolet light area. Further, it was found that the fluoroquinolone antibiotics may label the cells in the human body and it was verified that the fluoroquinolone antibiotics may label the bacteria and fungi. Accordingly, the present invention may provide the method of labeling the cells of the tissue in the human body and information on diagnosis of the infectious bacteria and fungi, by using the fluoroquinolone antibiotics.

As the fluoroquinolone antibiotics, there are moxifloxacin, gatifloxacin, pefloxacin, difloxacin, nofloxacin, ciprofloxacin, ofloxacin, enrofloxacin, and the like, but preferably, fluoroquinolone antibiotics in which auto-fluorescence is expressed in the visible light area or multi-photon fluorescence including the visible light area may be expressed are suitable. Hereinafter, in Experimental Example, the experiment was performed by using gatifloxacin and hydrochloride moxifloxacin substituted with hydrochloride which are frequently used as ocular antibiotics among the fluoroquinolone antibiotics.

In the following Experimental Example, it was verified that the hydrochloride moxifloxacin and the gatifloxacin may express fluorescent signals even in a light source having a near-infrared wavelength in a range of 700 nm to 800 nm.

Further, it was verified through the following Experimental Examples that fluorescence efficiency of the body tissue administered with the antibiotics is 10 to 100 times larger than the auto-fluorescence and images of antibiotics-based cells in the tissue may be photographed without removing the tissue.

The present invention may be applied to various at least one of the following: a biological tissue, bacteria, and fungi, and preferably, may be applied to cells in the tissue, for example, eye (cornea), skin, small intestine, stomach, cecum, colon, rectum, liver, lung, etc. In Experimental Example of the present invention, the fluorescence expression was measured by administering hydrochloride moxifloxacin and gatifloxacin to corneal cells, skin cells, and bladder cells.

In order to use the fluoroquinolone antibiotics in the method of diagnosing at least one of the infectious bacteria and fungi, only when causative bacteria or fungi existing in each cell as well as the cells in the tissue are labeled, whether infection exists or not may be determined. The method of the present invention may be applied to various at least one of bacteria and fungi, and preferably, may be applied to at least one of bacteria and fungi, and preferably which may be infected in the cells in the biological tissue. Further, the method of the present invention may be applied even to fungus consisting of eukaryotes such as a human.

In Experimental Example of the present invention, *pseudomonas* and *staphylococcus* were cultured, fluoroquinolone antibiotics were administered, and it was verified through the multi-photon microscope that the fluorescence was expressed.

First, moxifloxacin and gatifloxacin which are used in the experiment and areas and intensities of the fluorescence expression of the antibiotics will be described with reference to FIGS. 1, 2 and 3A to 3B.

The moxifloxacin as 0.5% of vigamox eye drops being sold in the market (Alcon Korea Co., Ltd.) is hydrochloride moxifloxacin (moxifloxacin HCl, 5.45 mg of hydrochloride moxifloxacin) synthesized with hydrochloride like a structural formula illustrated in FIG. 1.

Figure 2:
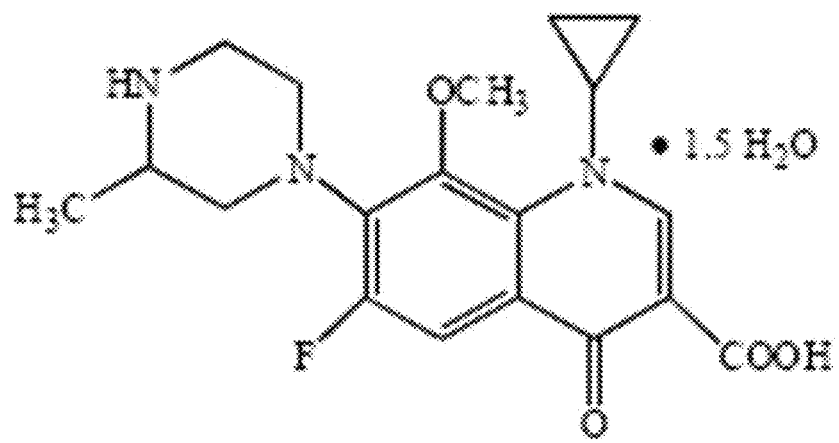
FIG. 2 illustrates a structural formula and a chemical formula of gatifloxacin used in the present invention.

The gatifloxacin is gatiflo eye drops (Handok pharmaceuticals Co., Ltd., 3 mg of gatifloxacin) having a structural formula illustrated in FIG. 2.

Figure 3A:
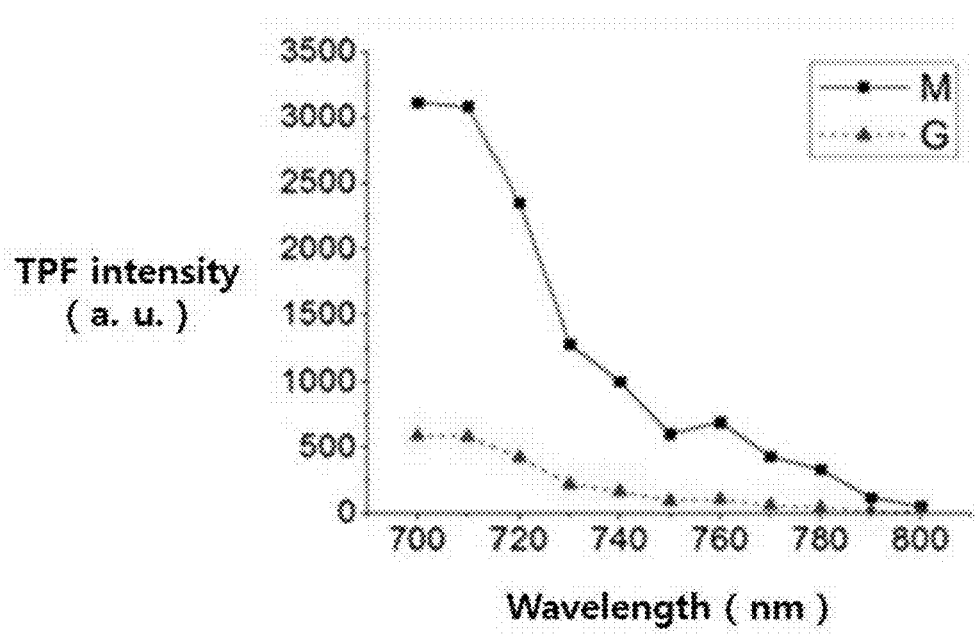
FIG. 3A illustrates an excite spectrum of hydrochloride moxifloxacin M and gatifloxacin G and FIG. 3B illustrates a fluorescence spectrum of hydrochloride moxifloxacin M and gatifloxacin G.

FIG. 3A illustrates an excitation spectrum of hydrochloride moxifloxacin and gatifloxacin. Here, an X axis represents a wavelength (nm) of a femtosecond laser light source used in the experiment, and a degree (a.u.) of two-photon excited fluorescence (TPF) at 700 nm to 800 nm which is a measuring range of a femtosecond laser wavelength is illustrated as a Y axis. Through the graph, it can be seen that hydrochloride moxifloxacin and gatifloxacin may represent fluorescent signals in the light source having a range of 700 nm to 800 nm which is a near-infrared wavelength. Further, in the case where the wavelength of the light source is 700 nm as shown in the intensity of the excited fluorescence graph of the Y axis, it can be seen that a fluorescent signal stronger than other wavelengths is shown.

Figure 3B:
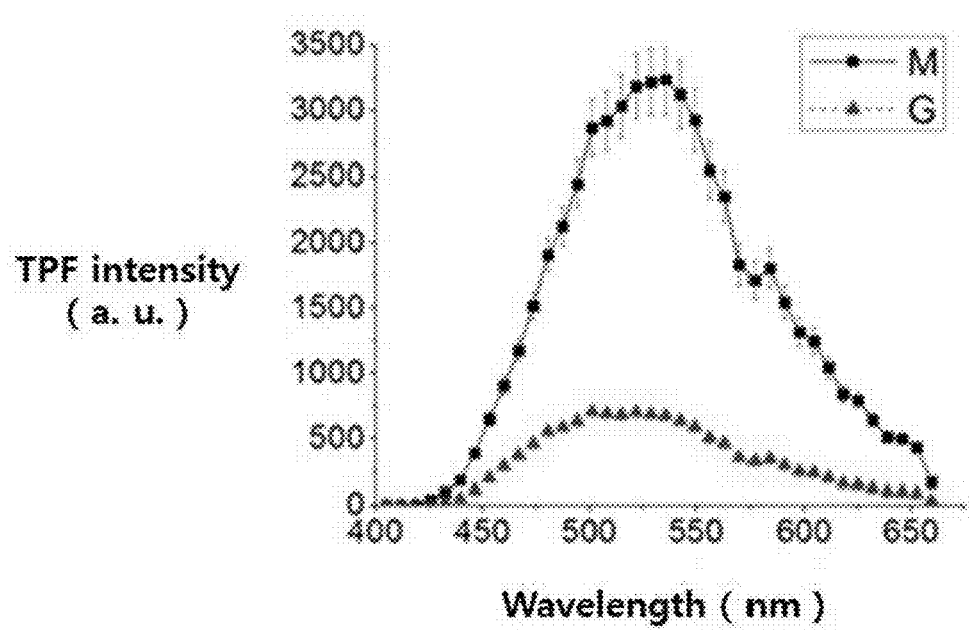

FIG. 3B illustrates an emission spectrum representing a fluorescence expression degree of each antibiotic when the femtosecond laser is applied to hydrochloride moxifloxacin and gatifloxacin. The X axis represents a wavelength (nm) and the Y axis represents the degree (a.u.) of the TPF. In the graph, in the hydrochloride moxifloxacin and the gatifloxacin, it can be seen that the fluorescent signals having wavelengths of 450 nm to 550 nm are frequently expressed and the wavelength of about 520 nm is expressed most strongly. Further, in the intensity of the graph of the Y axis, it can be seen that the fluorescence expression of the hydrochloride moxifloxacin is much better than that of the gatifloxacin.

Hereinafter, the present invention will be described in more detail through Experimental Examples. Experimental Examples are just to describe the present invention in more detail, and the scope of the present invention is not limited by Experimental Examples according to the gist of the present invention. In the following experiment, as cells of a tissue, a cornea, a skin (ears), and a bladder are targeted, but the present invention is not limited thereto, and may be applied to cells of various tissues in the body such as a prostate and a colon.

The bacteria target *pseudomonas* and *staphylococcus*, but the present invention may be applied to various bacteria which may be infected in cells of the tissue in the body, and is not limited to the following Experimental Examples. And the present invention may be applied to various fungi such as *aspergillus* and *candida*, and is not limited to the following Further, the present invention may be applied even to a fungus which is a eukaryote such as a human and is not limited even to a kind of fungus.

[Experimental Example 1]: Measurement of Multi-Photon Fluorescence of Corneal Cells of Fluoroquinolone Antibiotics (Hydrochloride Moxifloxacin and Gatifloxacin)

1) Preparation of Materials and Samples

Blab/c female mice after five or six weeks, gatifloxacin, hydrochloride moxifloxacin, and a multi-photon microscope including a biaxial scanner (a galvano scanner of x axis and a galvano scanner of y axis) to be used by a point scanning method were prepared.

In this Experimental Example, a two-photon microscope using a femtosecond laser as a light source was used and the multi-photon fluorescence was equally measured under the following condition throughout an experimental process.

Excitation wavelength: 780 nm for vigamox (moxifloxacin)
Filter set: Ch01:[430 nm, Ch02:]430 nm
Manufacturer/Product name of Microscope: Leica/TCS SP5II MP SMD FLIM
Filter: 500/25 bandpass filter, chroma
Light source: chameleon vision II, coherent
Camera: photon multiplier tube (PMT) 6357, Hamamatsu Photonics
Objective lens: 25×0.95 NA objective lens, leica 2) Measurement of Multi-Photon Fluorescence of Corneal Cells of Fluoroquinolone Antibiotics (Hydrochloride Moxifloxacin and Gatifloxacin)

In order to compare fluorescence expression of hydrochloride moxifloxacin with auto-fluorescence expression of the corneal cells of the mouse, the corneal cells of the mouse which are not applied with hydrochloride moxifloxacin were first photographed.

The Blab/c mouse to be used in the experiment was anesthetized and then fixed to an eye holder for photographing the eye, and photographed by the two-photon microscope. Laser power was set as 30.8 mW, and in this case, the intensity of auto-fluorescence of the photographed mouse cornea was recorded.

In order to measure the fluorescence expression degree of the mouse cornea by vigamox (hydrochloride moxifloxacin), hydrochloride moxifloxacin of 10 µl was dropped in a left eye of the mouse and an eyelid was closed for 30 seconds.

About 20 minutes waited so that hydrochloride moxifloxacin may penetrate into cells inside the mouse cornea.

An incubation time when the antibiotic penetrates varies according to a tissue, but was verified by photographing with for example, a time lapse such as after 5 minutes and after 10 minutes. In the cornea, the incubation time was within about several tens of minutes. The fluorescence image of the cornea was photographed by the point scanning method through the two-photon microscope. (In this case, an excitation wavelength of the spectrum was set as 790 nm, the laser power of the hydrochloride moxifloxacin was about 14.8 mW, and the laser power of the gatifloxacin was set as 30.8 mW which was the same as the laser power before administering the antibiotic.

FIG. 4A to 4E illustrate photographs of a cornea of a left eye of a mouse which is not treated with hydrochloride moxifloxacin and gatifloxacin photographed by an X-Y plane point scanning method using the two-photon microscope and average signal graphs.

FIGS. 4A to 4D illustrate appearances in which hydrochloride moxifloxacins administered to a corneal superficial epithelial cell layer, a corneal basal epithelial cell layer, a corneal stroma layer, and a corneal endothelium layer are fluorescent-expressed, respectively. Here, a yellow solid line represents a scale bar and a length means 100 μm.

Figure 4A:
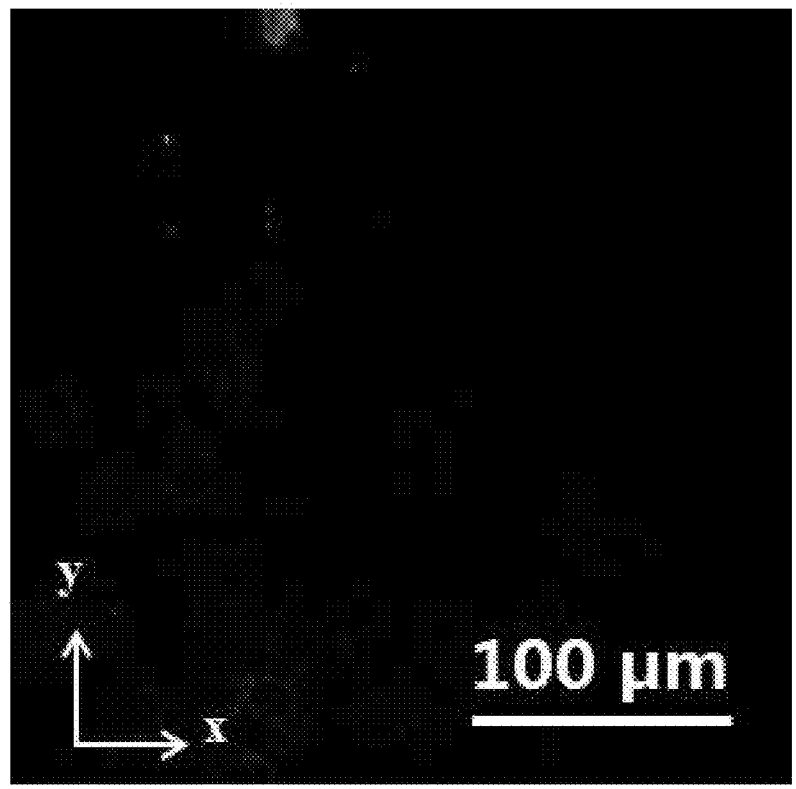
FIGS. 4A to 4D illustrate auto-fluorescence expression photographs of a corneal superficial epithelium, a corneal basal epithelium, a corneal stroma, and a corneal endothelium of a mouse, respectively.
Figure 4B:
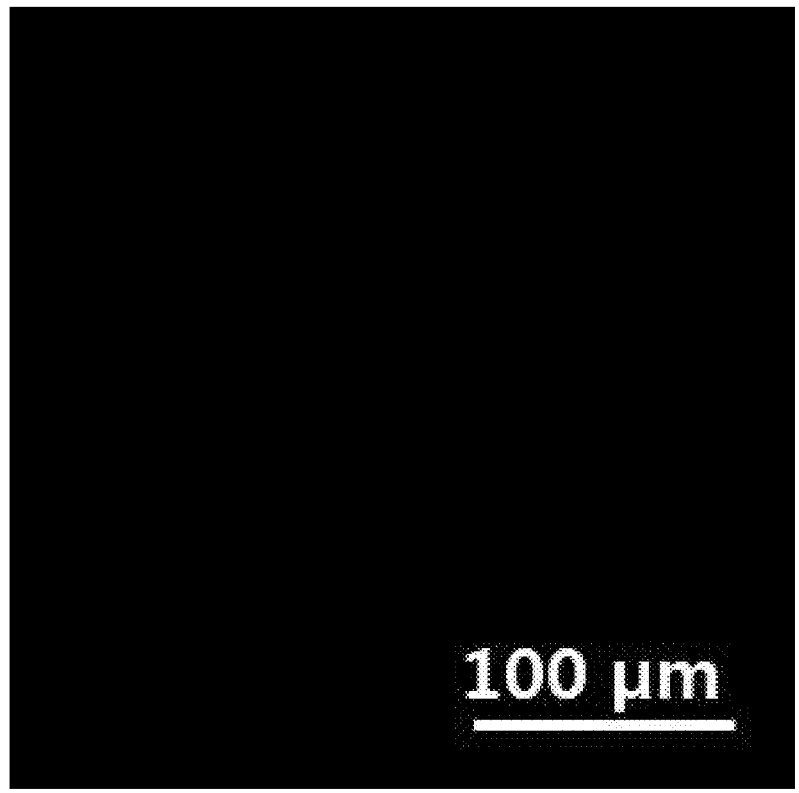
Figure 4C:
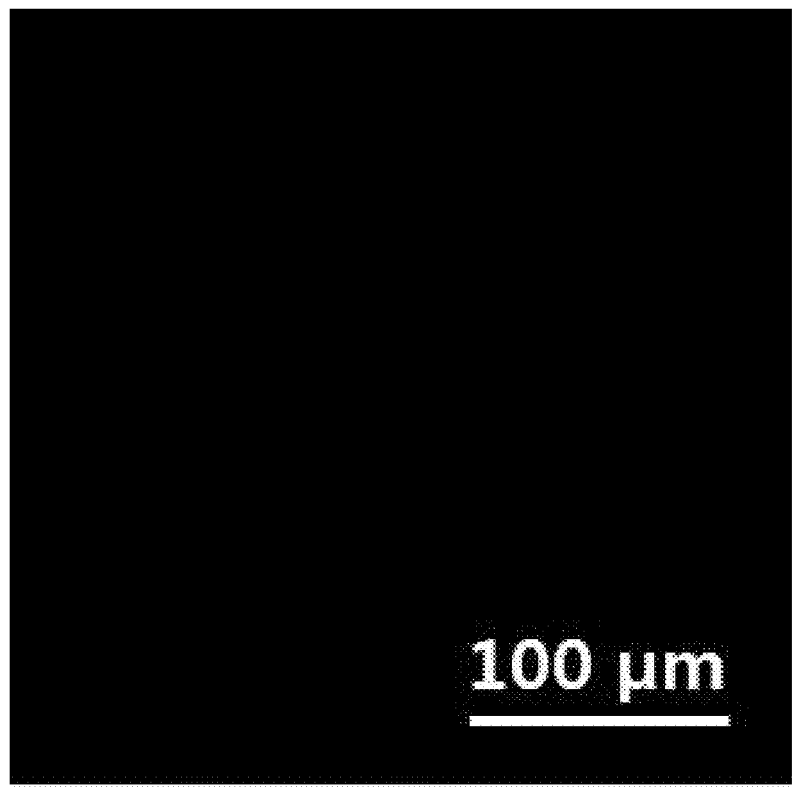
Figure 4D:
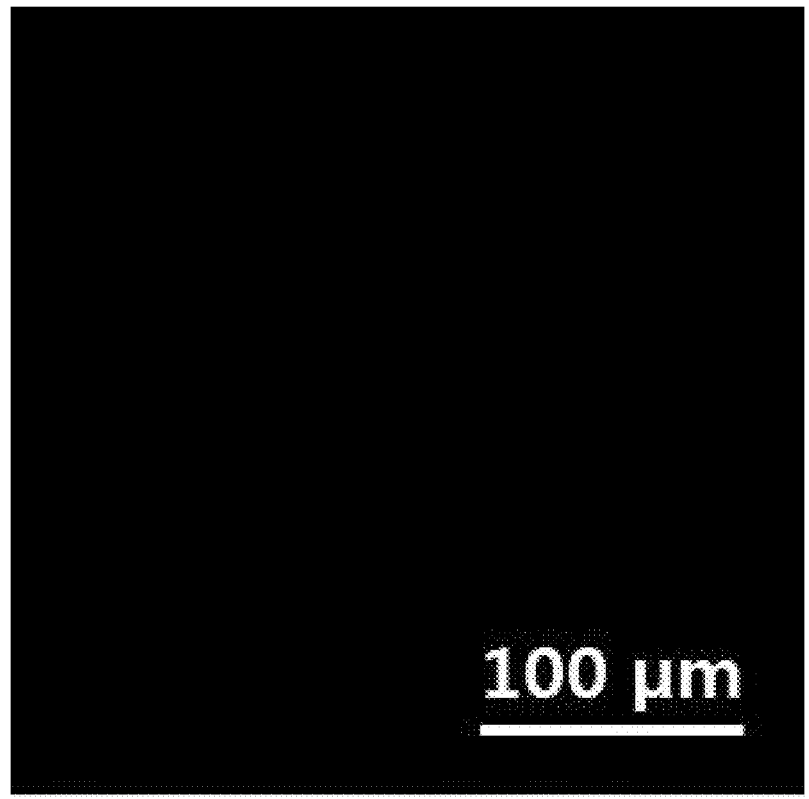
Figure 4E:
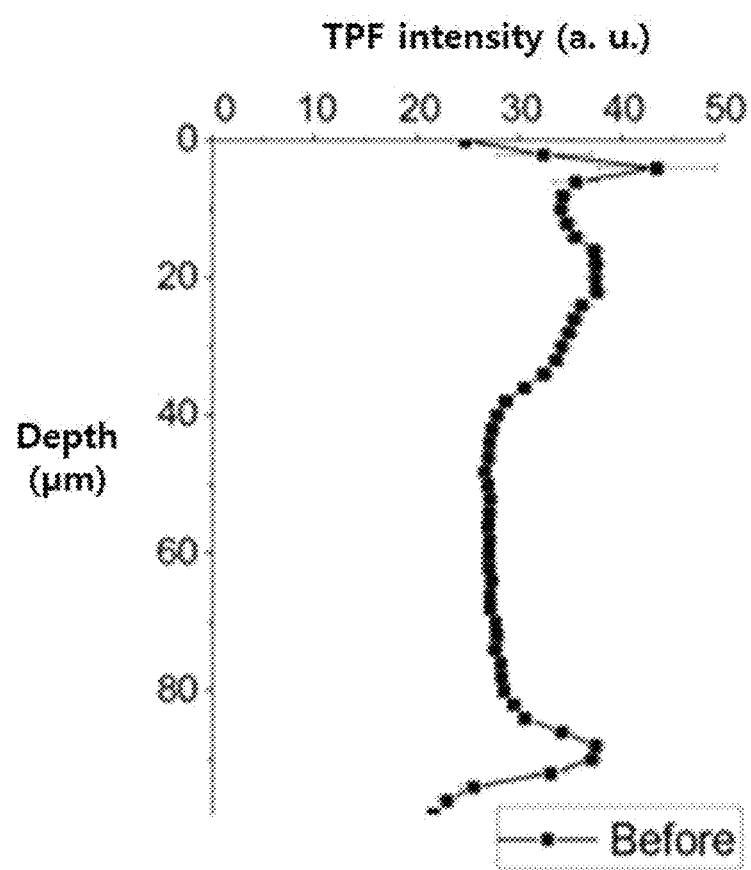
FIG. 4E illustrates an average signal graph of FIGS. 4A to 4D.

FIG. 4E illustrates an average signal graph at positions of each cornea which is fluorescent-expressed while descending from a position of FIG. 4A to a position of FIG. 4D, and an X axis represents the intensity of a signal in a depth direction from a surface to the corneal endothelium layer in depth. That is, a depth of 0 is a corneal surface and means the corneal epithelial layer, the stroma, and the corneal endothelium layer downwards.

In the photographs illustrated in FIGS. 4A to 4D, it can be seen that the auto-fluorescence expression in the body tissue is very weak in the laser power of 30.8 mW, and in this case, it can be seen that a size of the fluorescent signal is significantly low as 20 to 50 a.u. as verified in a graph of FIG. 4E.

Figure 5A:
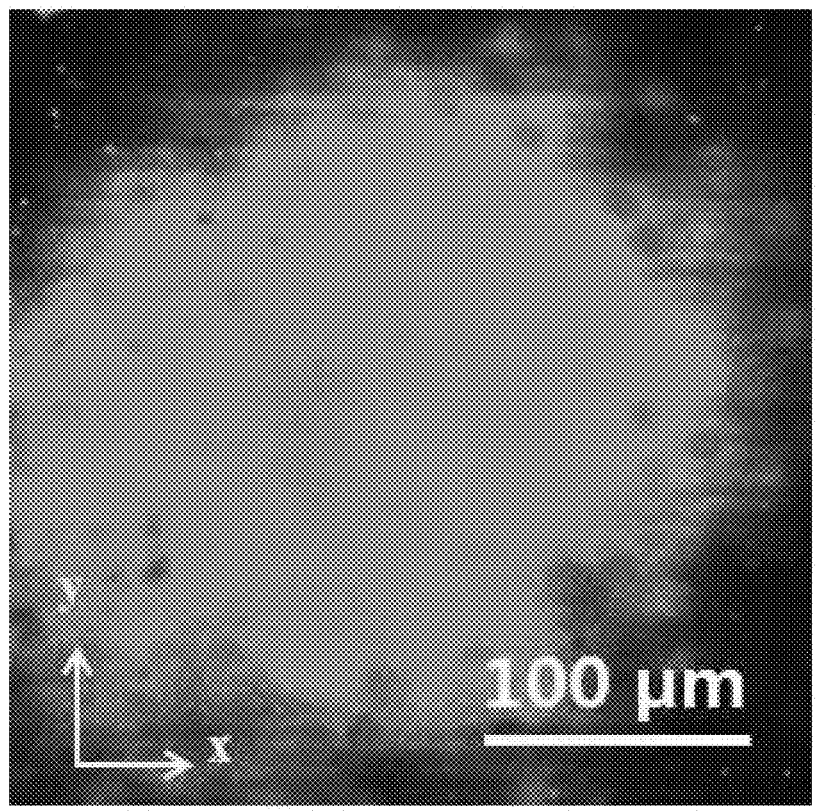
FIGS. 5A to 5D are photographs fluorescent-expressed by administering hydrochloride moxifloxacin to the cornea of the mouse, respectively.
Figure 5B:
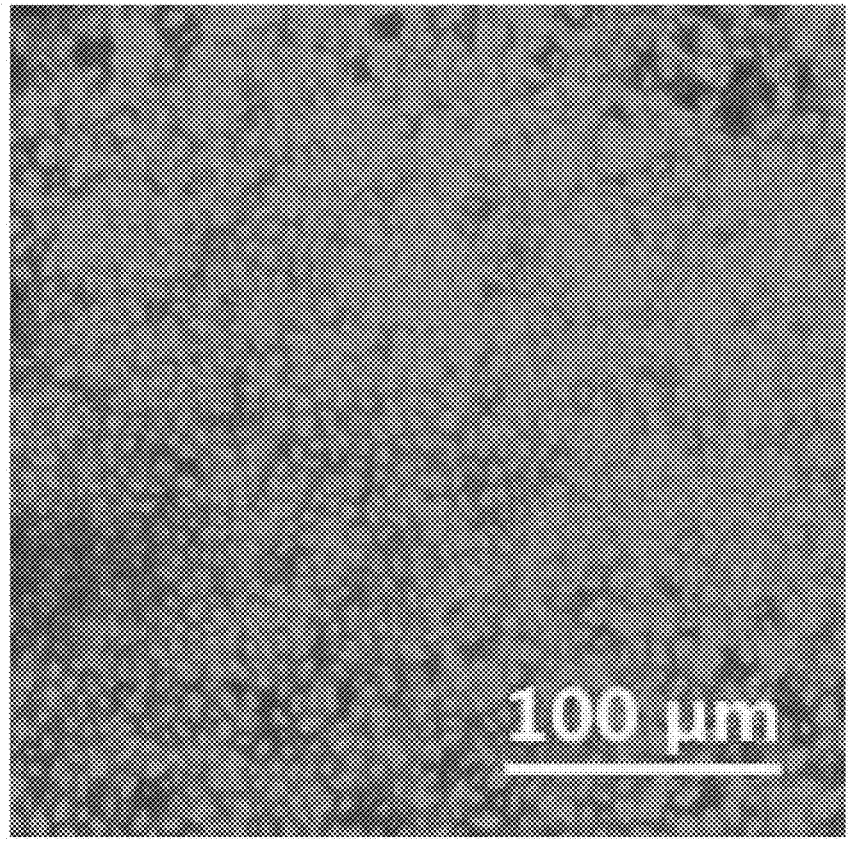
Figure 5C:
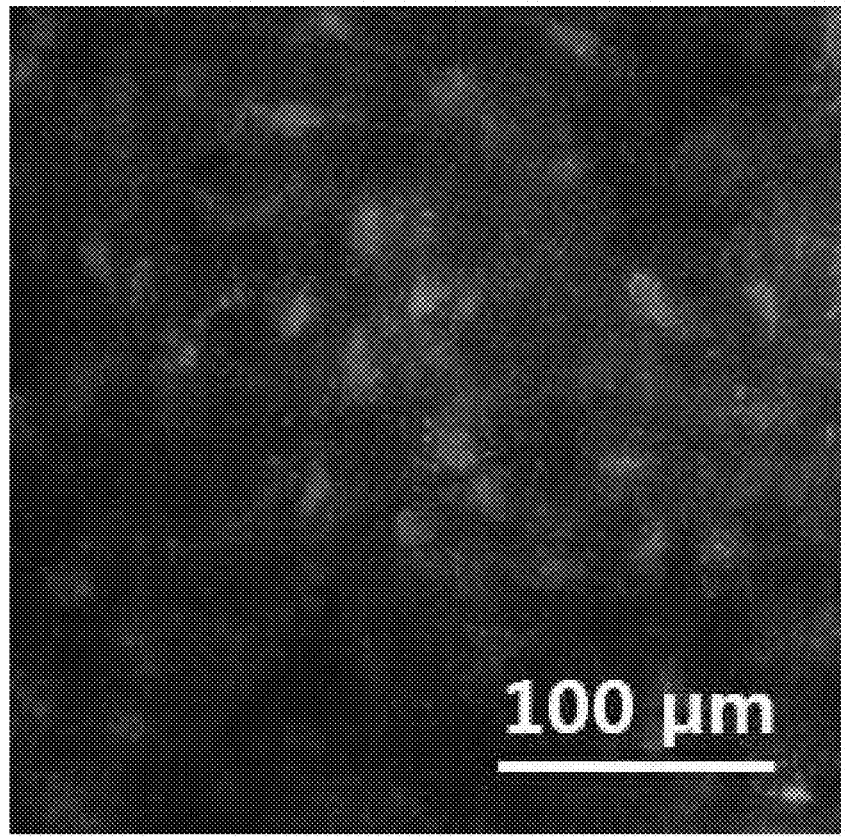
Figure 5D:
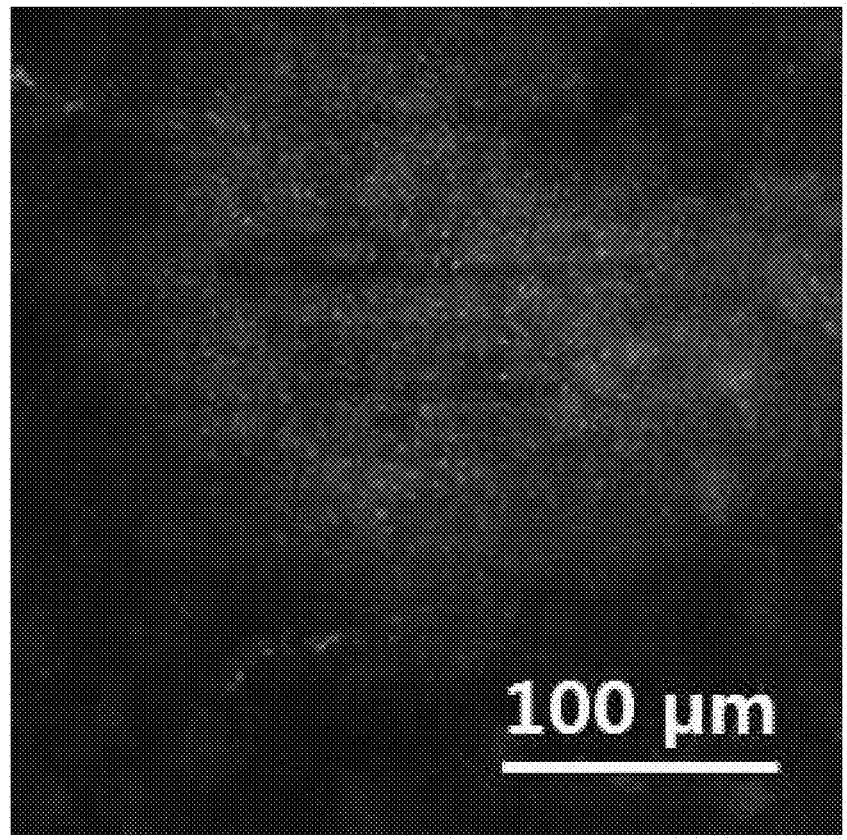
Figure 6A:
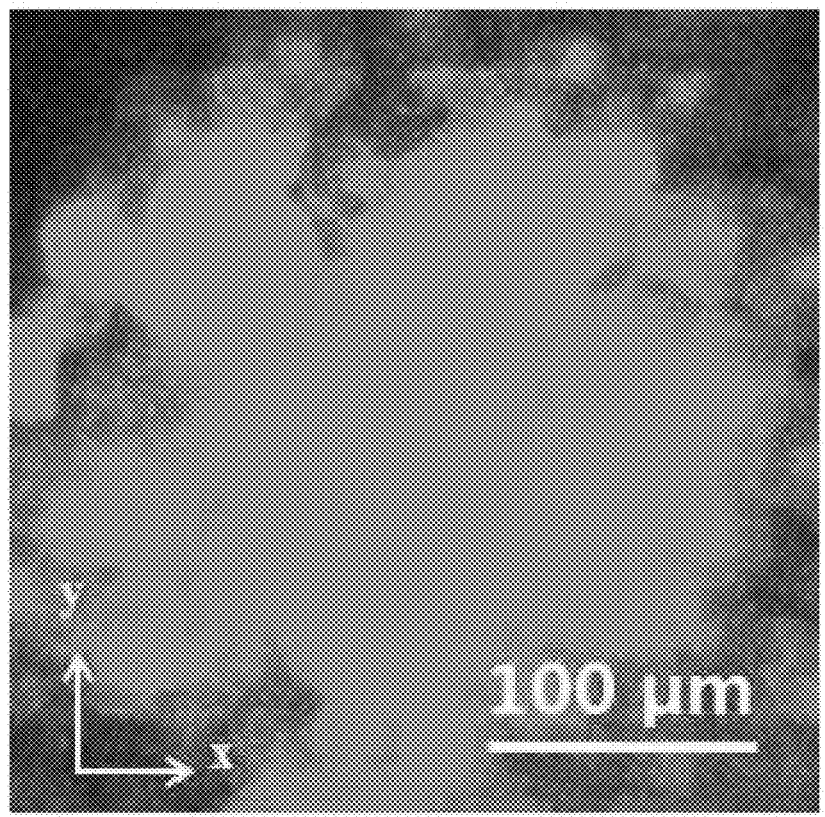
FIGS. 6A to 6D are photographs fluorescent-expressed by administering gatifloxacin to the cornea of the mouse, respectively.
Figure 6B:
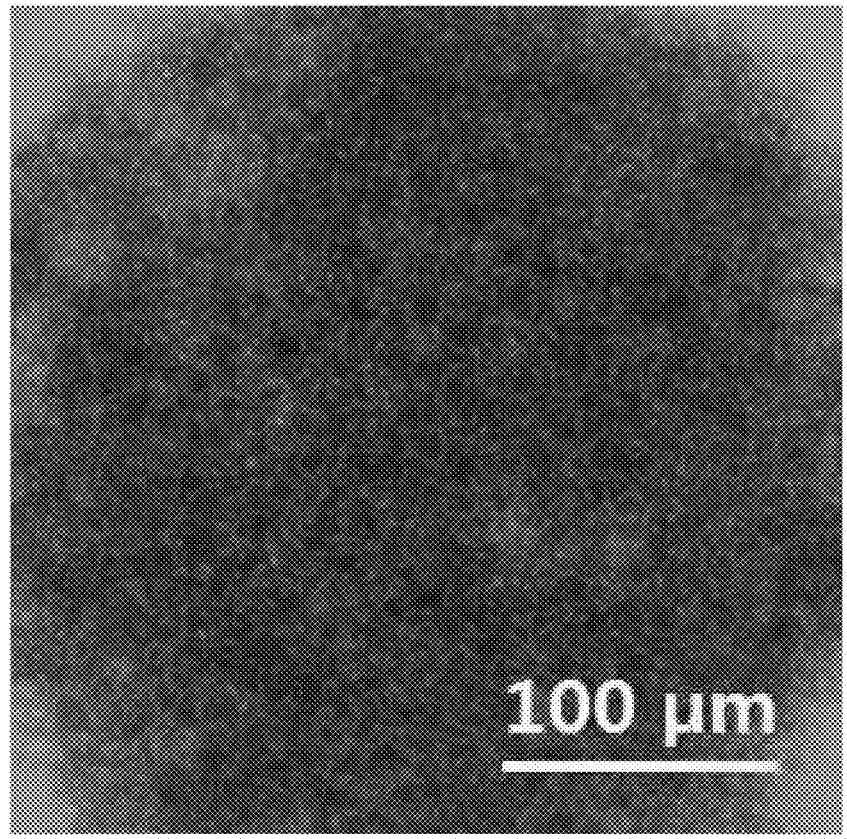
Figure 6C:
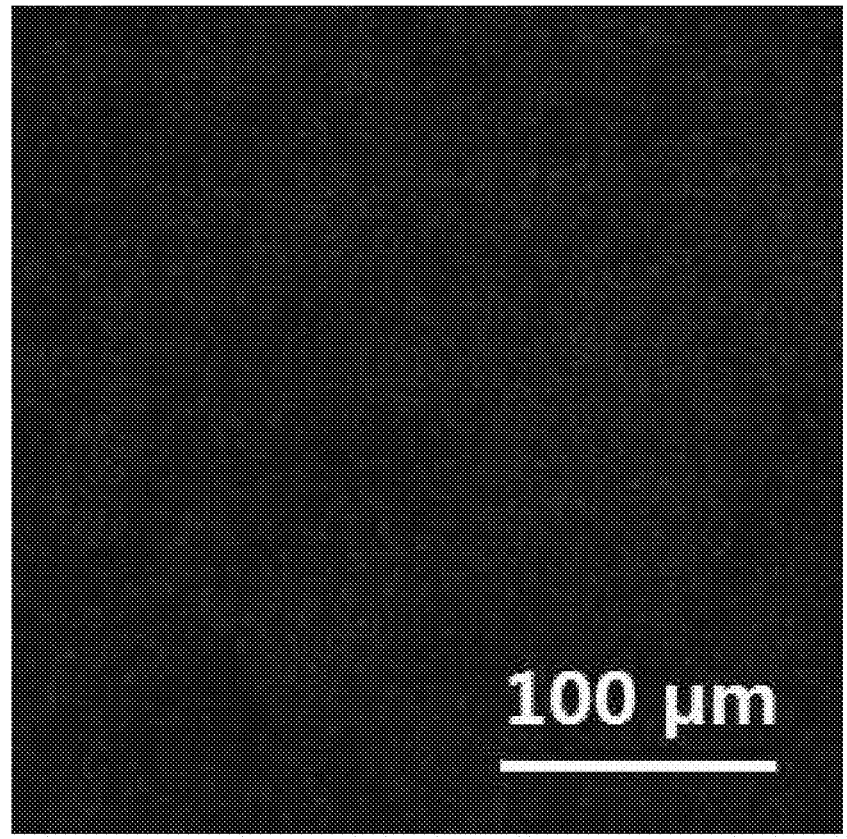
Figure 6D:
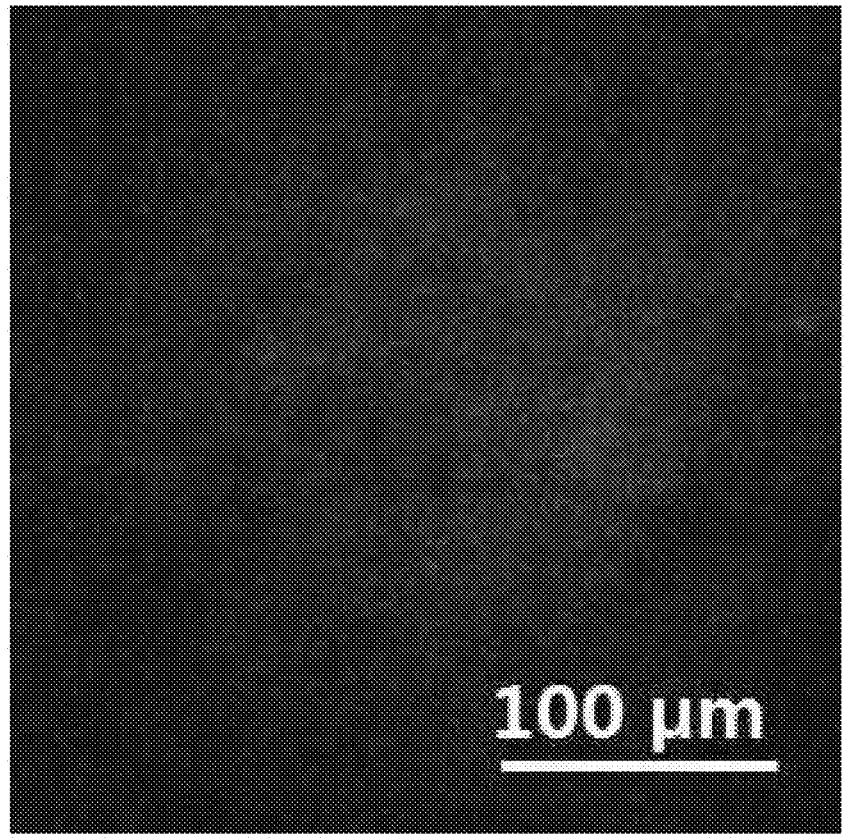

FIGS. 5A and 5D are photographs photographing the fluorescent-expressed cornea of the mouse by hydrochloride moxifloxacin through a multi-photon microscope. And FIGS. 6A and 6D are photographs photographing the fluorescent-expressed cornea of the mouse by gatifloxacin through a multi-photon microscope. Here, FIGS. 5A and 6A illustrate appearances of the corneal superficial epithelial cell layer, FIGS. 5B and 6B illustrate appearances of the corneal basal epithelial cell layer, FIGS. 5C and 6C illustrate appearances of the corneal stroma layer, FIGS. 5D and 6D illustrate appearances of the corneal endothelium layer, which are fluorescent-expressed on an X-Y plane, respectively. Here, a yellow solid line represents a scale bar and a length means 100 μm.

In a concentration difference of fluorescent colors illustrated in FIGS. 5A to 5D and 6A to 6D, it can be seen that there is a difference in fluorescence expression due to fluoroquinolone antibiotics (hydrochloride moxifloxacin and gatifloxacin). It is verified that the fluorescence expression degree is strongly shown on the corneal superficial epithelial cell layers of FIGS. 5A and 6A which are the corneal surfaces because the fluoroquinolone antibiotics are dropped from the corneal epithelial layer to be diffused and penetrate to the inside of the cornea.

Figure 5E:
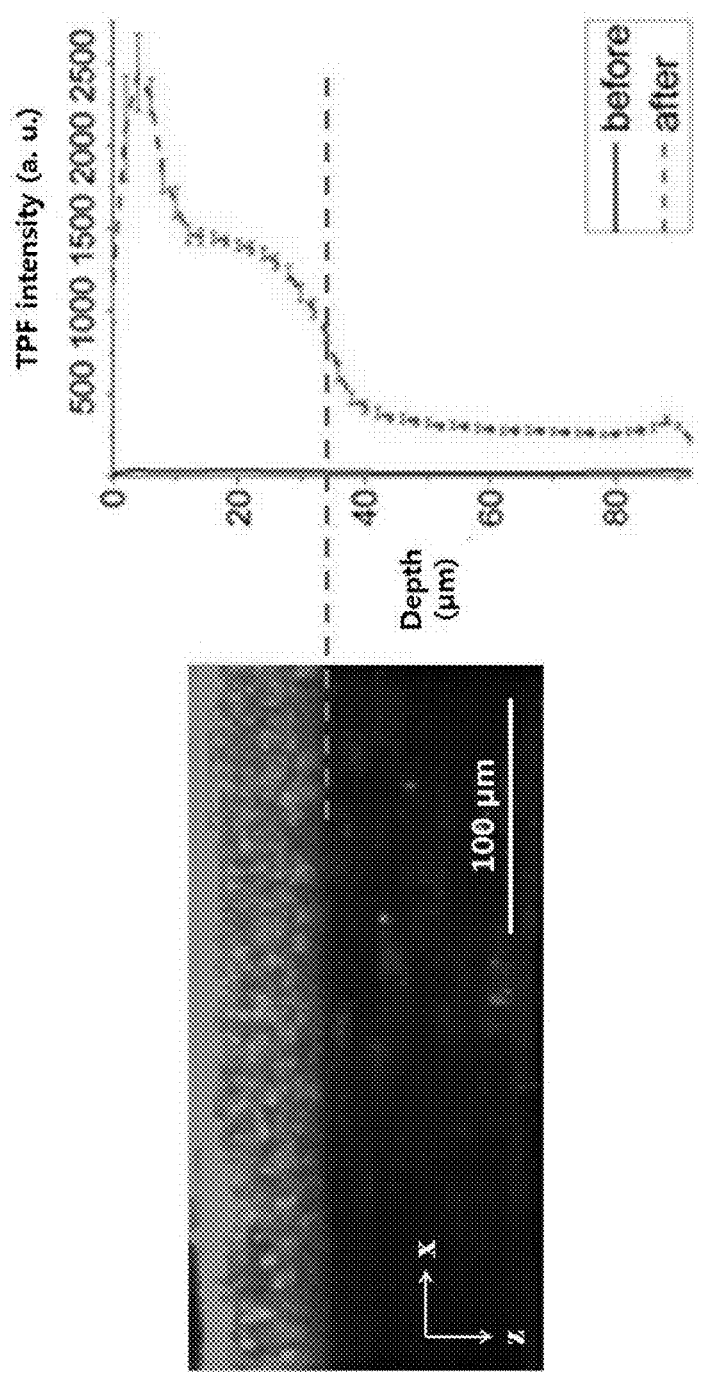
FIGS. 5E and 6E illustrate tomograms and average signal graphs of the superficial epithelium, the basal epithelium, the stroma, and the endothelium administered with hydrochloride moxifloxacin and gatifloxacin, respectively.
Figure 6E:
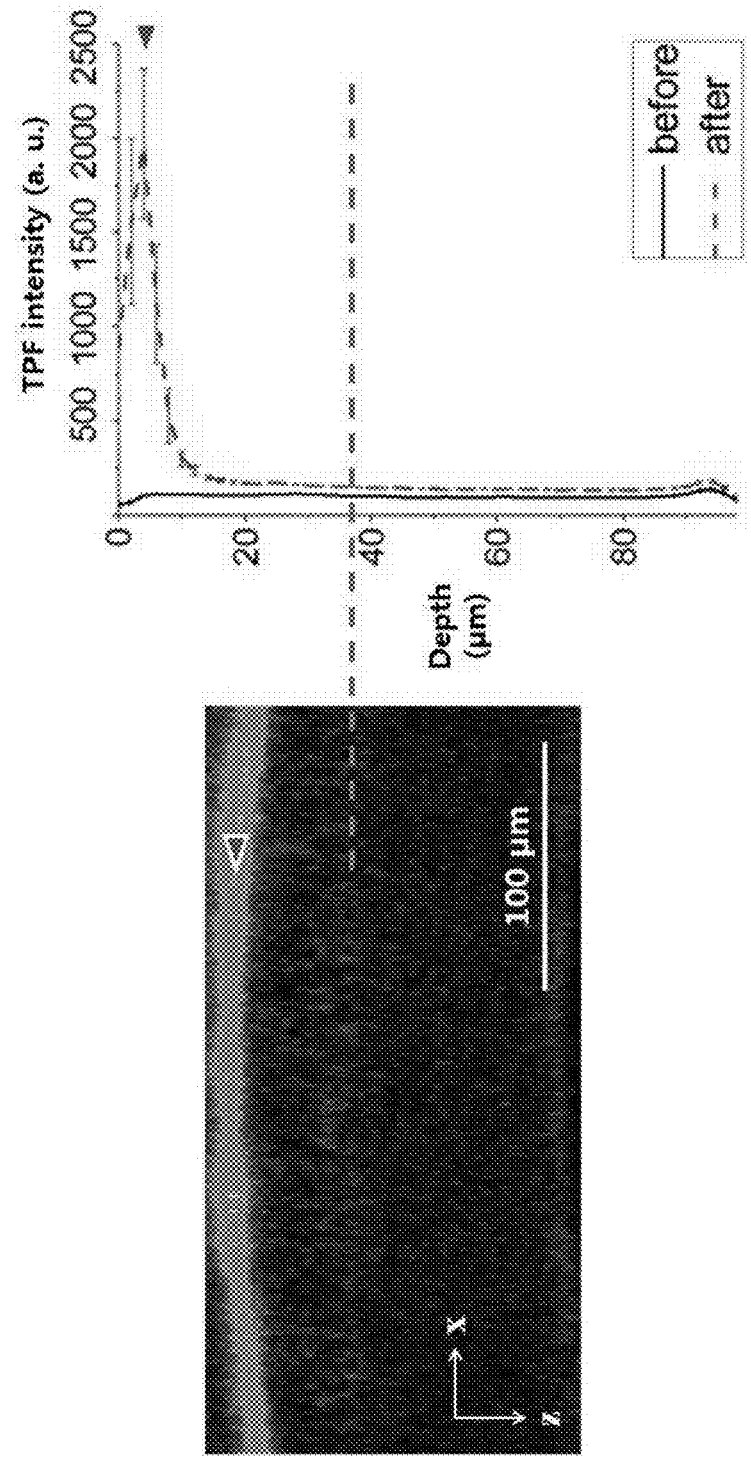
Figure 7A:
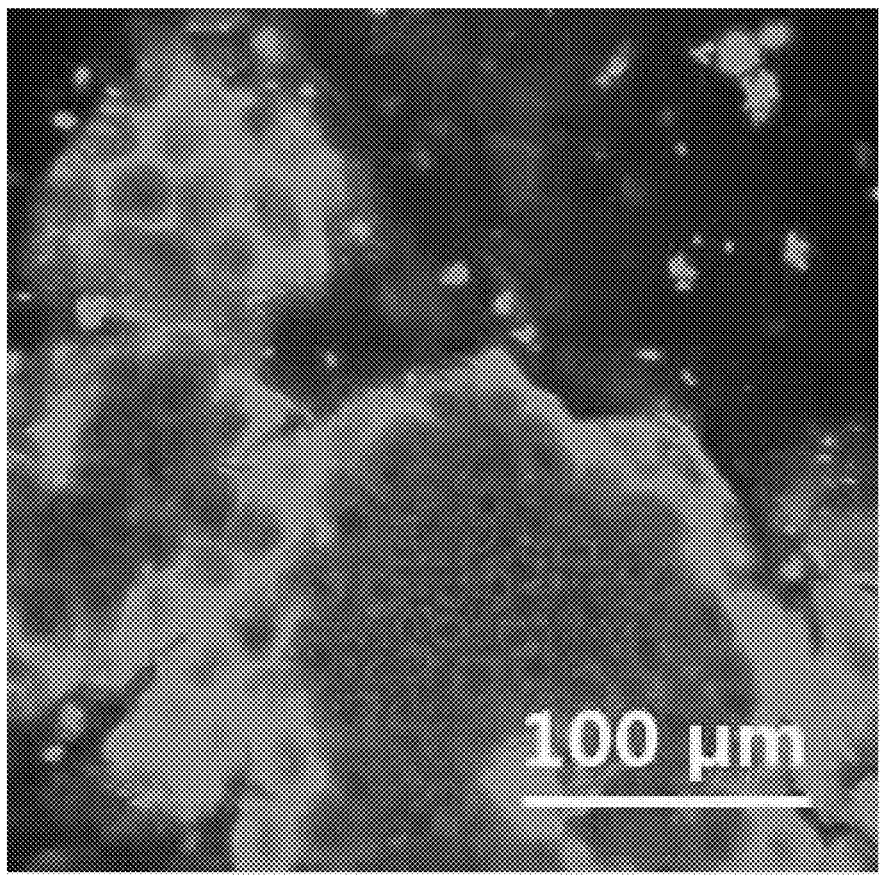
FIGS. 7A to 7D are auto-fluorescence expressed photographs photographed by a two-photon microscope while descending from epithelia cells to dermal cells of a ear skin of a mouse.
Figure 7B:
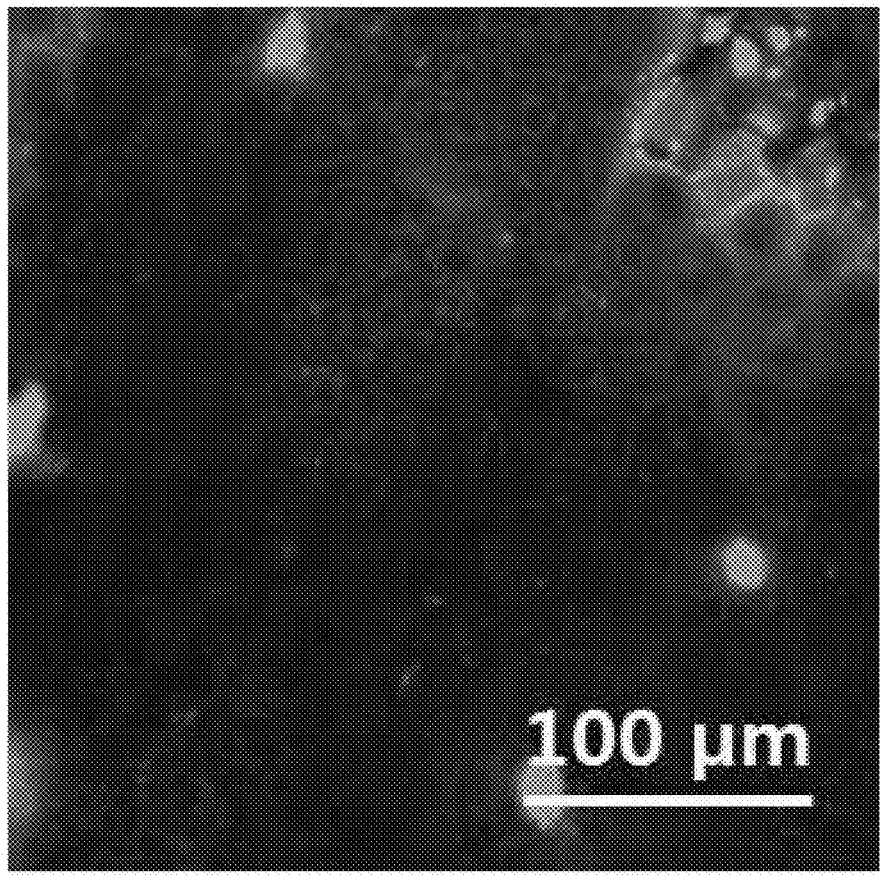
Figure 7C:
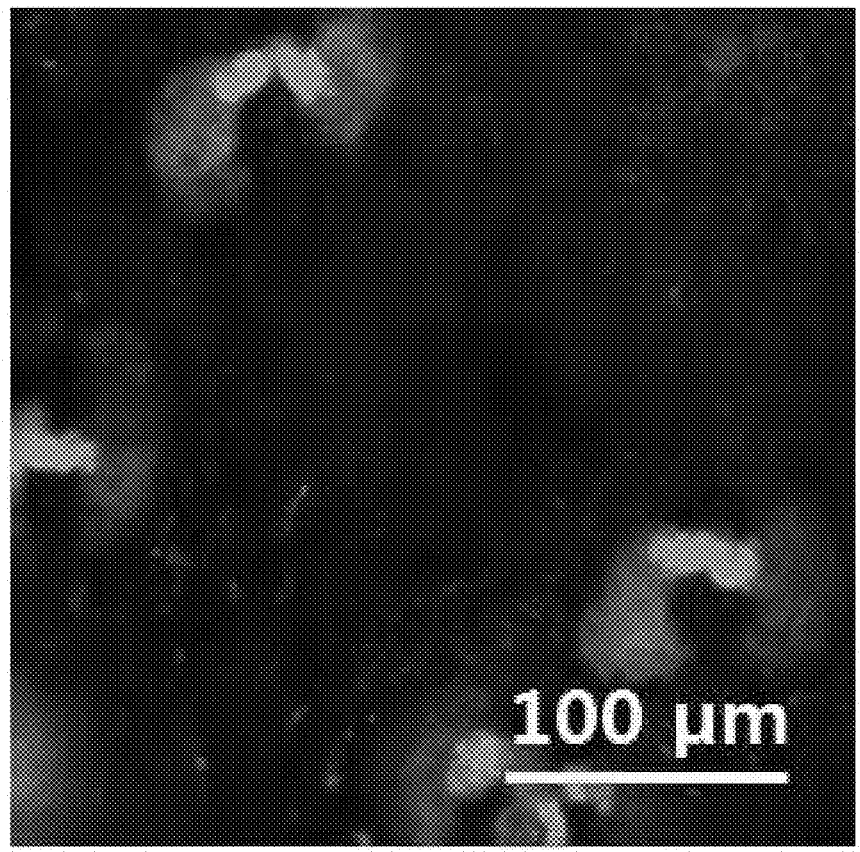
Figure 7D:
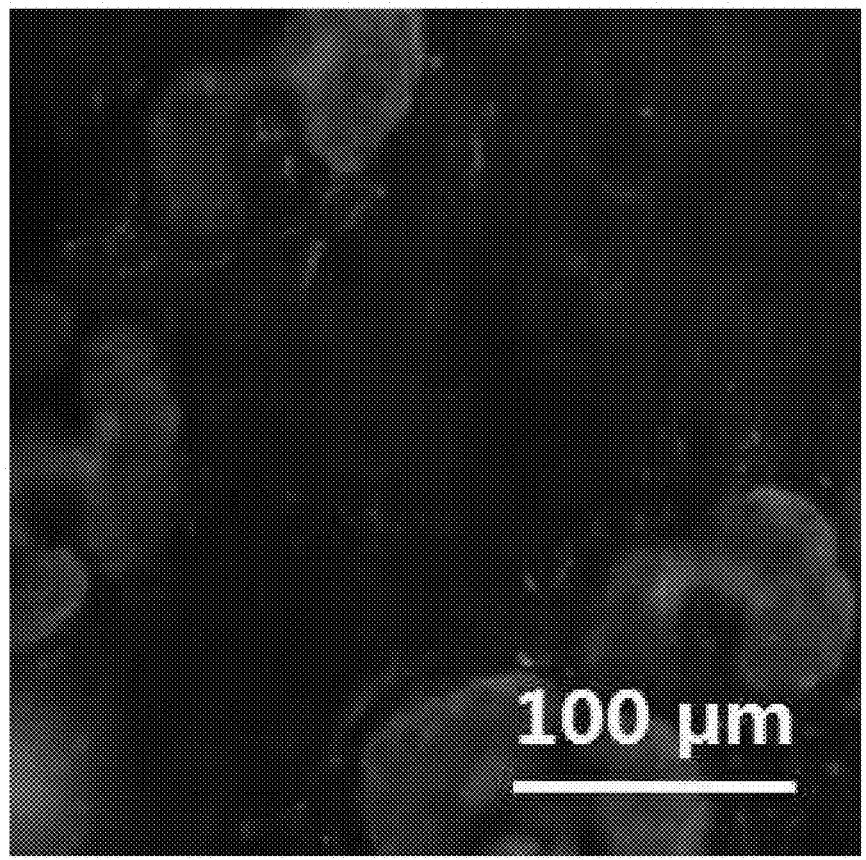
Figure 8A:
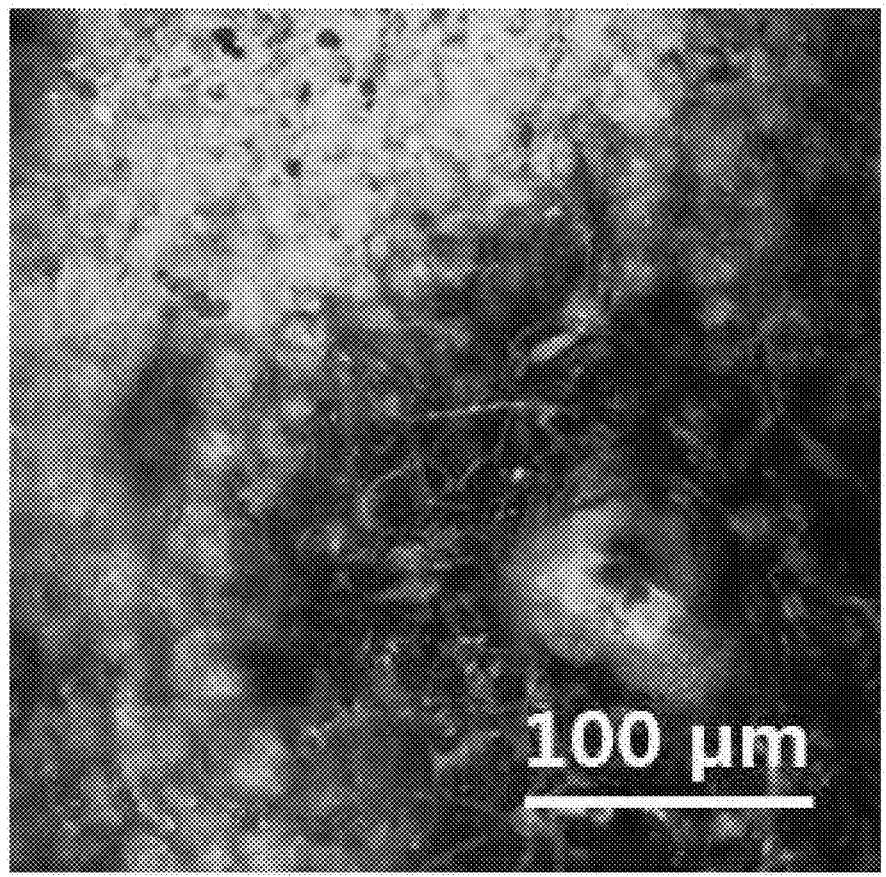
FIGS. 8A to 8D are photographs fluorescent-expressed at the same position of FIGS. 7A to 7D by administering hydrochloride moxifloxacin, respectively.
Figure 8B:
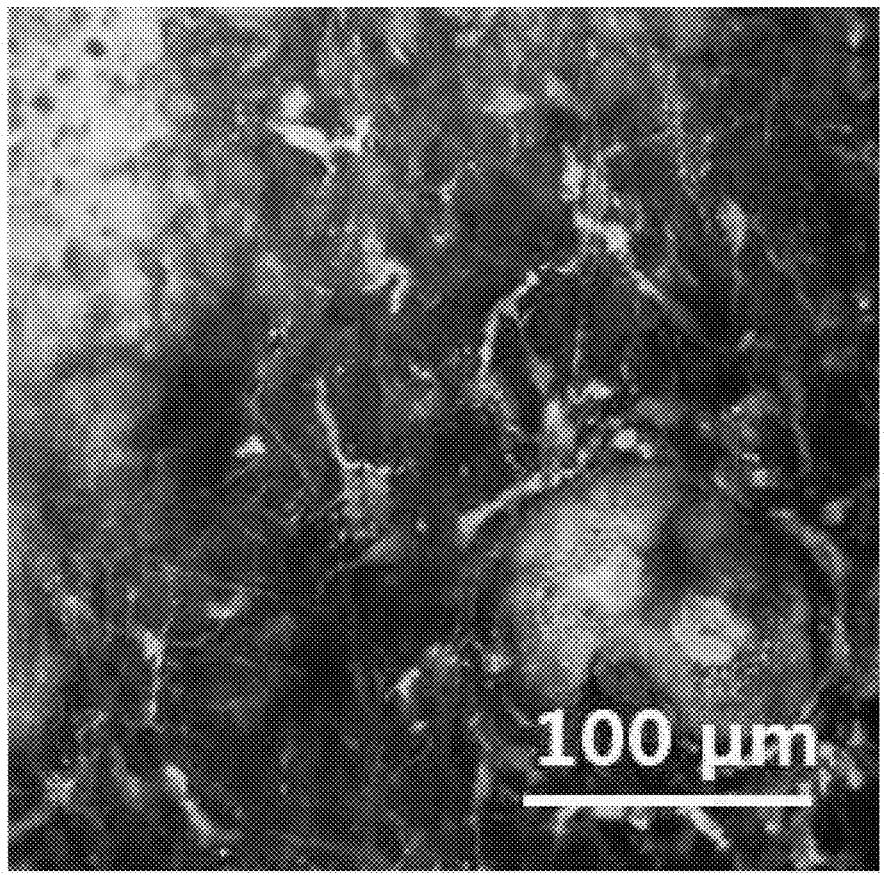
Figure 8C:
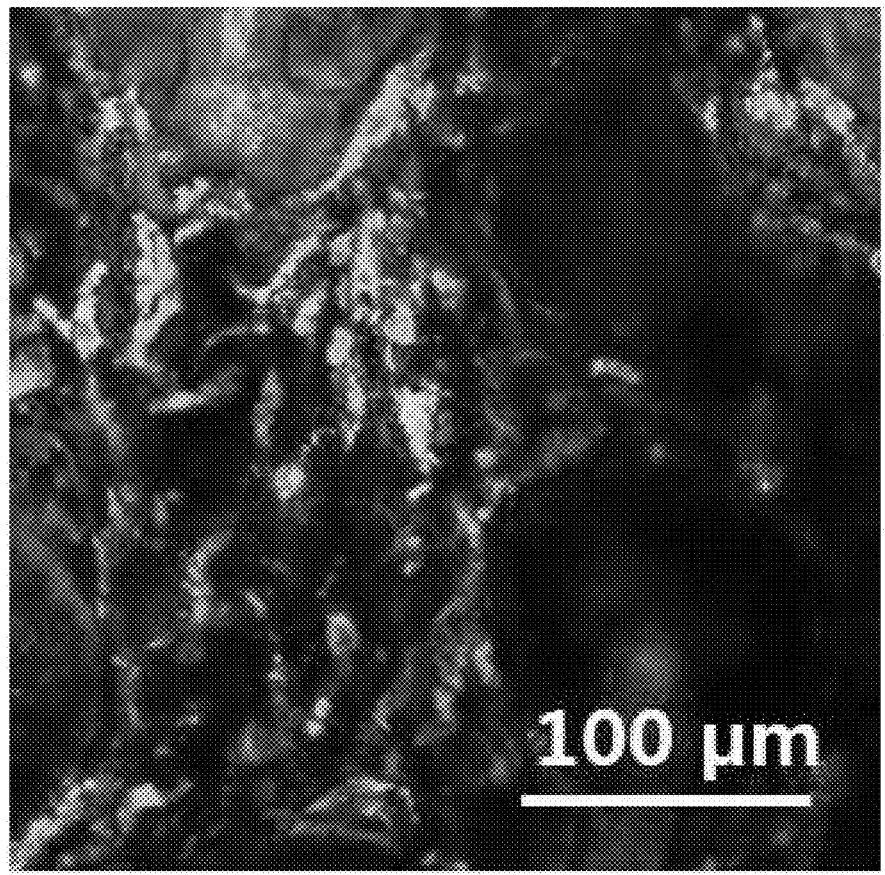
Figure 8D:
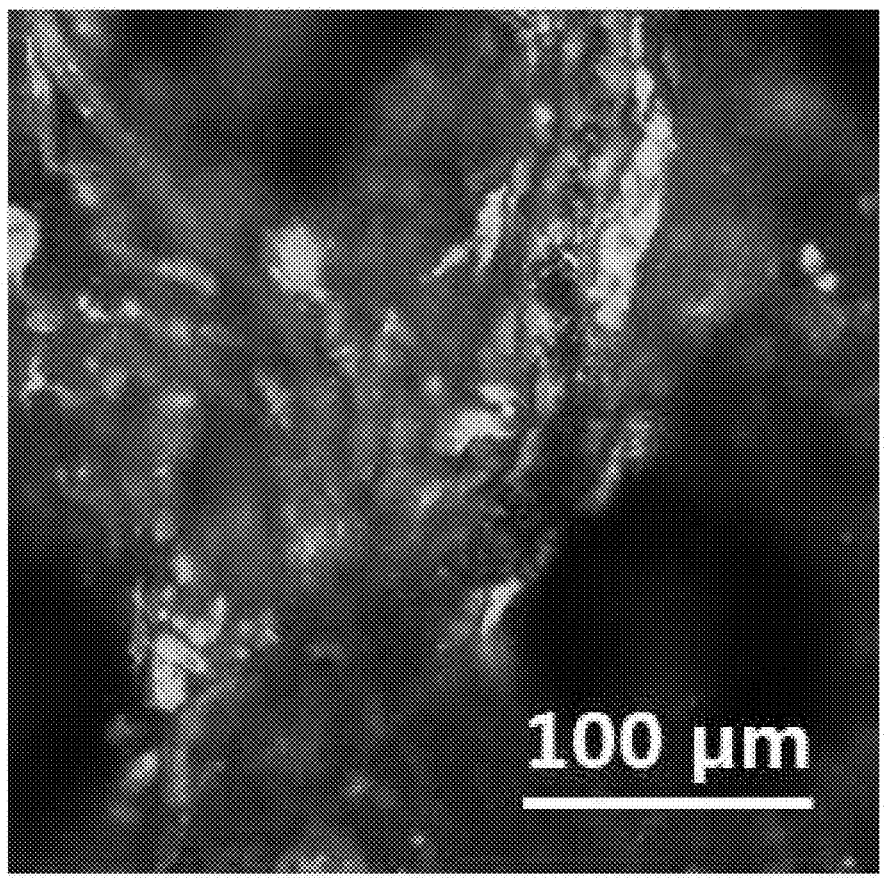

FIGS. 5E and 6E illustrate photographs photographing the cornea labeled with hydrochloride moxifloxacin through point scanning on an X-Z plane and an X-axial depth represents the intensity of a signal in a depth direction from the surface to the corneal endothelium layer. That is, the top of the X axis represents the corneal epithelial layer and represents the corneal endothelium layer downwards. In this photograph, it is verified that the fluorescence expression is strongly shown on the superficial epithelial cell layer. And in graphs, the depth of 0 means the corneal surface, and a depth represented by a blue dotted line of the graph means a thickness of the entire corneal epithelial layer, and lower portions thereof mean the stroma layer and the corneal endothelium layer, respectively.

When comparing FIGS. 4A to 4D and 6A to 6D as the same laser power condition of 30.8 mW, it can be seen that the intensity of the fluorescence expression when administering the gatifloxacin is much larger than that of the auto-fluorescence expression. Further, in the case of the hydrochloride moxifloxacin, even in the laser power of 14.8 mW, the intensity of the signal is larger than that of the auto-fluorescence expression and the fluorescence expression by the gatifloxacin of the mouse cornea which are measured with 30.8 mW, and as a result, it can be seen that the fluorescence expression is very excellent during administration to the cornea.

Further, when comparing graphs of FIGS. 5E and 6E and a graph of FIG. 4E, even in the corneal endothelium layer, it can be seen that the fluorescence intensity when administering the hydrochloride moxifloxacin and the gatifloxacin is higher than the fluorescence intensity of the auto-fluorescence expression. As a result, it can be seen that the innermost cell layer in the tissue may be verified by the fluorescence expression signal through the hydrochloride moxifloxacin and the gatifloxacin.

Hereinafter, in Experimental Examples, an experiment was performed by using only hydrochloride moxifloxacin of which fluorescence expression is better than that of gatifloxacin.

[Experimental Example 2]: Measurement of Multi-Photon Fluorescence in Skin Cells of Hydrochloride Moxifloxacin 1) Preparation of Materials and Samples Blab/c female mice after five or six weeks, hydrochloride moxifloxacin, and a two-photon microscope including a biaxial scanner (a galvano scanner of x axis and a galvano scanner of y axis) to be photographed by a point scanning method, a scotch tape, a PBS were prepared.

In this Experimental Example, a two-photon microscope using a femtosecond laser as a light source was used and the multi-photon fluorescence was equally measured under the following condition throughout an experimental process.

Excitation wavelength: 780 nm for vigamox (moxifloxacin)
    Filter set: Ch01: [490 nm, Ch02:]490 nm
    Light source: Chameleon Ultra II, Coherent
    Camera: photomultiplier tube (PMT) H7421-40P, Hamamatsu Photonics
    Objective lens: 20×1.0 NA objective lens, XLUMPIanFL, Olympus
    Photographing area: 300 μm×300 μm (512×512 pixels)

2) Measurement of Multi-Photon Fluorescence in Skin Cells of Hydrochloride Moxifloxacin In order to compare fluorescence expression of hydrochloride moxifloxacin with auto-fluorescence expression of the skin cells of the mouse, the skin cells of the mouse which are not applied with hydrochloride moxifloxacin were first photographed by the two-photon microscope. While the mouse was alive through inhalation anesthesia, a skin (ear) tissue was photographed.

In order to photograph the fluorescence expression of the hydrochloride moxifloxacin in the skin tissue of the mouse, a general scotch tape was repeatedly attached to and detached from the ear tissue of the mouse about 15 times to remove a horny layer and vigamox was applied.

After the vigamox penetrated for about 20 minutes, the vigamox was washed by using the PBS, and while the mouse was alive through inhalation anesthesia like the pre-photographing of the vigamox, the image of the skin (ear) tissue was photographed by the point scanning method through the multi-photon microscope.

FIGS. 7A to 7D illustrate auto-fluorescence expressed photographs of an ear tissue of a mouse before administering hydrochloride moxifloxacin photographed while descending from superficial epithelial cells to dermal cells, respectively, and FIGS. 8A to 8D are fluorescence expressed photographs of the ear tissue at the same position after administering hydrochloride moxifloxacin photographed by the same method, respectively. In this case, the power of the used laser was 121 mW before administering the hydrochloride moxifloxacin and 17 mW after administering the hydrochloride moxifloxacin.

When describing the fluorescence expression degrees of FIGS. 7A to 7D and 8A to 8D, it can be seen that the fluorescence expression is excellent around the superficial epithelial cells and the intensity of the fluorescent signal is decreased toward the dermal cell.

Further, when comparing FIGS. 8A to 8D with FIGS. 7A to 7D at the same position, even though the laser power is significantly low, it can be seen that the tissue administered with the hydrochloride moxifloxacin was clearly photographed. Particularly, when comparing FIGS. 7D and 8D as the innermost dermal cells, it could be seen that cells which are not shown by the auto-fluorescence expression, particularly, spatial dendritic cells (langerhans cells) were clearly observed by the fluorescence expression having the strong intensity of the hydrochloride moxifloxacin.

[Experimental Example 3]: Measurement of Multi-Photon Fluorescence in Bladder Cells of Hydrochloride Moxifloxacin 1) Preparation of Materials and Samples Hydrochloride moxifloxacin, a rat (normal), a vigamox eye drop (hydrochloride moxifloxacin), an anesthetics, a warmer, a slide glass, a forcep, a PBS, and a two-photon microscope including a biaxial scanner (a galvano scanner of x axis and a galvano scanner of y axis) to be used by a point scanning method for measuring the multi-photon fluorescence expression degree were prepared.

In this Experimental Example, the used vigamox and the two-photon microscope using a femtosecond laser as a light source were measured under the following specification condition throughout an experimental process.

Excitation wavelength: 780 nm for vigamox (moxifloxacin)
Filter set: Ch01: [490 nm, Ch02:]490 nm
Light source: Chameleon Ultra II, Coherent
Camera: photomultiplier tube (PMT) H7421-40P, Hamamatsu Photonics
Objective lens: 20×1.0 NA objective lens, XLUMPlanFL, Olympus
Photographing area: 300 μm×300 μm (512×512 pixels)—FIGS. 10A and 10B 150 μm×150 μm (512×512 pixels)—FIGS. 11A to 11C, 12A to 12C, 13A to 13C and 14A to 14c 2) Measurement of Multi-Photon Fluorescence in Bladder Cells of Hydrochloride Moxifloxacin In order to compare fluorescence expression of hydrochloride moxifloxacin with auto-fluorescence expression of the bladder cells of the mouse, the rat (normal) which was not applied with hydrochloride moxifloxacin was prepared and the bladder cells of the rat (normal) were first photographed by the two-photon microscope.

The rat (normal) was sacrificed and the bladder tissue was extracted. After the extracted bladder tissue was washed in a PBS solution about five times, the washed bladder tissue was cut with scissors for surgery and unfolded so that photographed portions (the lumen and the serosa) may be exposed outside. After the unfolded bladder tissue was placed on the slide glass so that the photographed portions (the lumen and the serosa) faced upward, covered with a coverslip, and fixed well (using a tape), the auto-fluorescence intensity was measured.

In Experimental Example, the auto-fluorescence intensity was measured while the objective lens descended by 2 μm so as to verify an appearance of cells photographed for each depth of the lumen and serosa tissues of the bladder tissue. Particularly, the lumen tissue was photographed so that the umbrella cell, the intermediate cell, and the laminar propria were verified, respectively.

Even like this Experimental Example, the incubation time when the antibiotic penetrated was photographed and verified with a time lapse. The fluorescence image of the bladder was photographed by the point scanning method through the two-photon microscope. In this experiment, in the lumen of the bladder tissue, the laser power of 300 mW or more was used, and in the serosa, the laser power of 200 mW or more was used.

Figure 9:
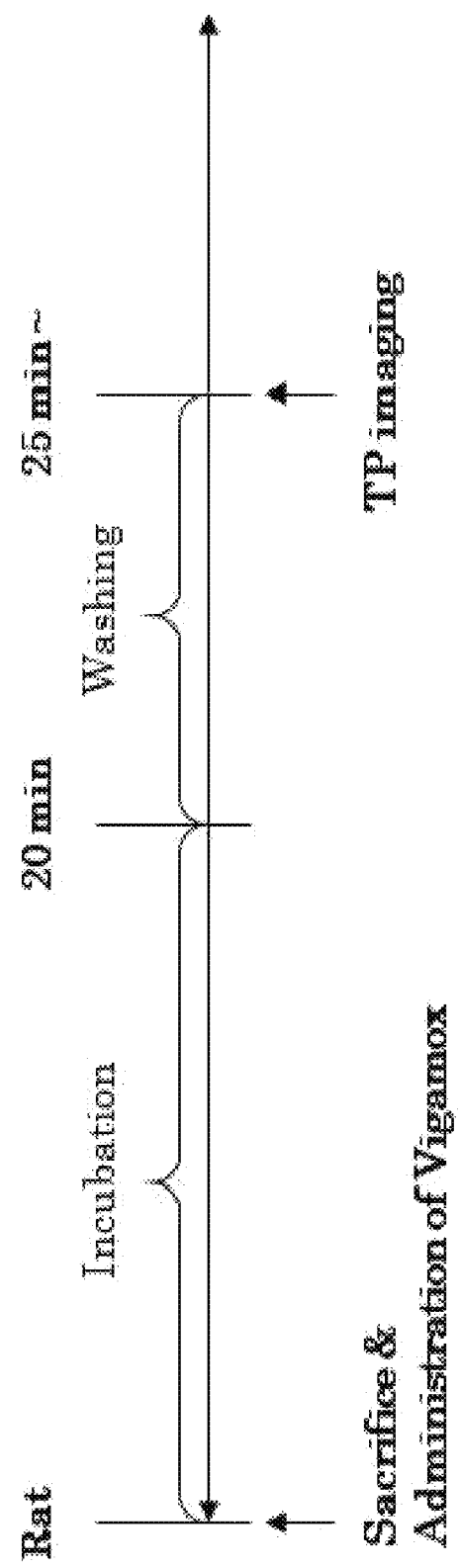
FIG. 9 illustrates a protocol of a fluorescence expression experiment of bladder cells of the mouse administered with the hydrochloride moxifloxacin.

Hereinafter, an experimental process of the multi-photon fluorescence measurement of the bladder cells administered with hydrochloride moxifloxacin will be described with reference to FIG. 9.

The rat normal was sacrificed, the bladder tissue was extracted, and the extracted tissue was immersed in vigamox (hydrochloride moxifloxacin) for 20 minutes and incubated. Thereafter, the bladder tissue was held with the forceps and gently washed while being shaken about 2 to 3 times in the PBS.

Thereafter, a tissue sample was prepared on the slide glass so that the lumen tissue which is the inside of the cell and the serasa tissue which is the outside of the cell are exposed during photographing and TPM-photographed within 30 minutes after the vigamox was treated so as to complete the photographing when the cells are activated.

Even like this Experimental Example, the incubation time when the antibiotic penetrated was photographed and verified with a time lapse. The fluorescence image of the bladder was photographed by the point scanning method through the two-photon microscope. In the lumen tissue of the bladder tissue treated with the hydrochloride moxifloxacin, the laser power of 15 mW was used, and in the serosa tissue, the laser power of 10 mW was used.

Figure 10A:
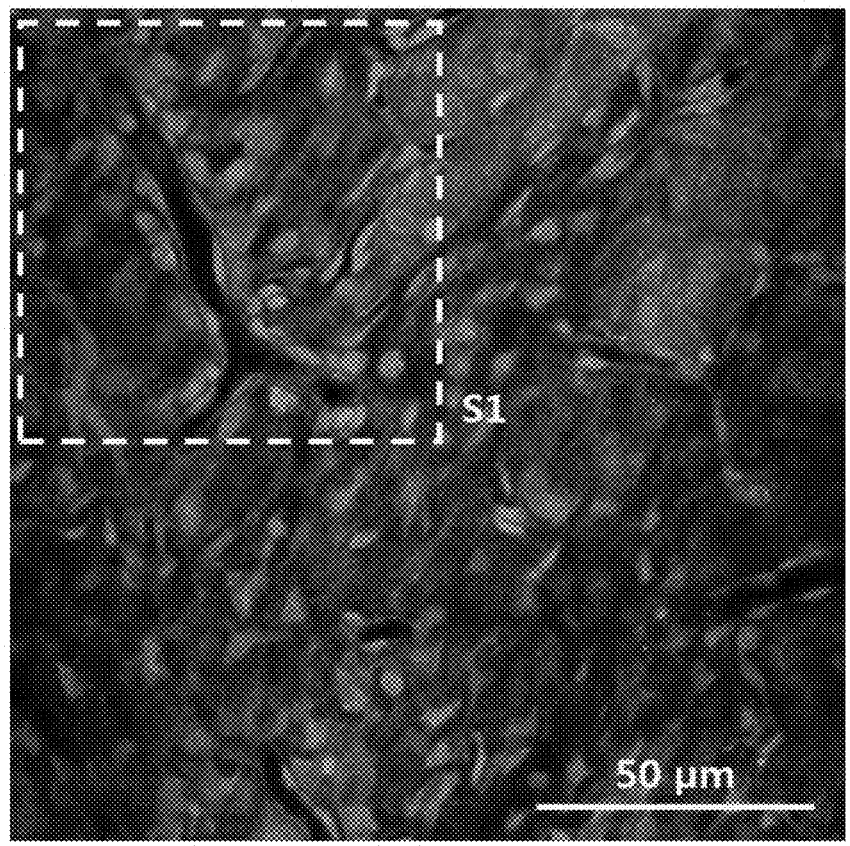
FIG. 10A illustrates a photograph fluorescent-expressed by administering hydrochloride moxifloxacin to a lumen tissue of the bladder and FIG. 10B illustrates a photograph fluorescent-expressed by administering hydrochloride moxifloxacin to a serosa tissue thereof.
Figure 10B:
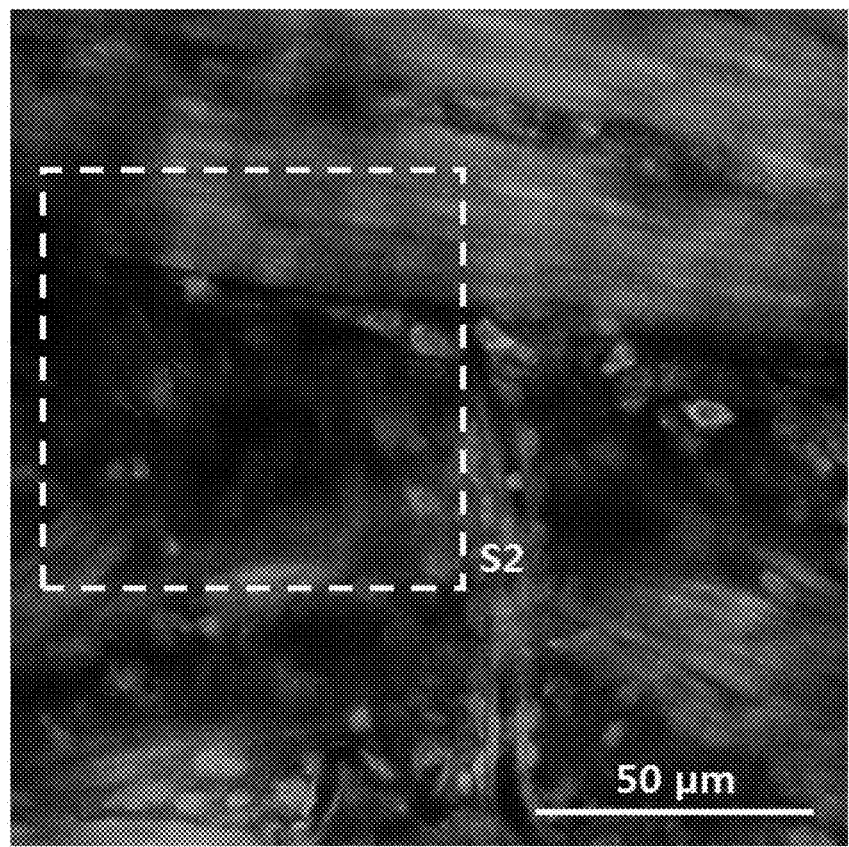

FIG. 10A is a photograph of a lumen of the bladder tissue of the mouse and FIG. 10B is a photograph of a serosa of the bladder tissue of the mouse, which are administered with hydrochloride moxifloxacin photographed by a two-photon microscope in an area of 300 μm×300 μm, respectively.

In the lumen of the bladder tissue of FIG. 10A, it could be seen that vascular endothelial cells arranged along a vascular wall were labeled and observed.

Even in the serosa of the bladder tissue of FIG. 10B, it can be seen that a muscle observed to be horizontally thick on the top of the photograph and cells existing between muscular tissues were observed. Further, it could be seen that the vascular endothelial cells and the cells distributed around the vascular endothelial cells were labeled and observed together.

More effectively, in order to observe expression of the hydrochloride moxifloxacin in the cells of the bladder tissue, it will be described in detail with reference to FIGS. 11A to 11C, 12A to 12C, 13A to 13C and 14A to 14C.

FIGS. 11A to 11C and 12A to 12C illustrate S1 of FIG. 10A as the inside of the bladder cell which are enlarged at 150 μm×150 μm.

Figure 11A:
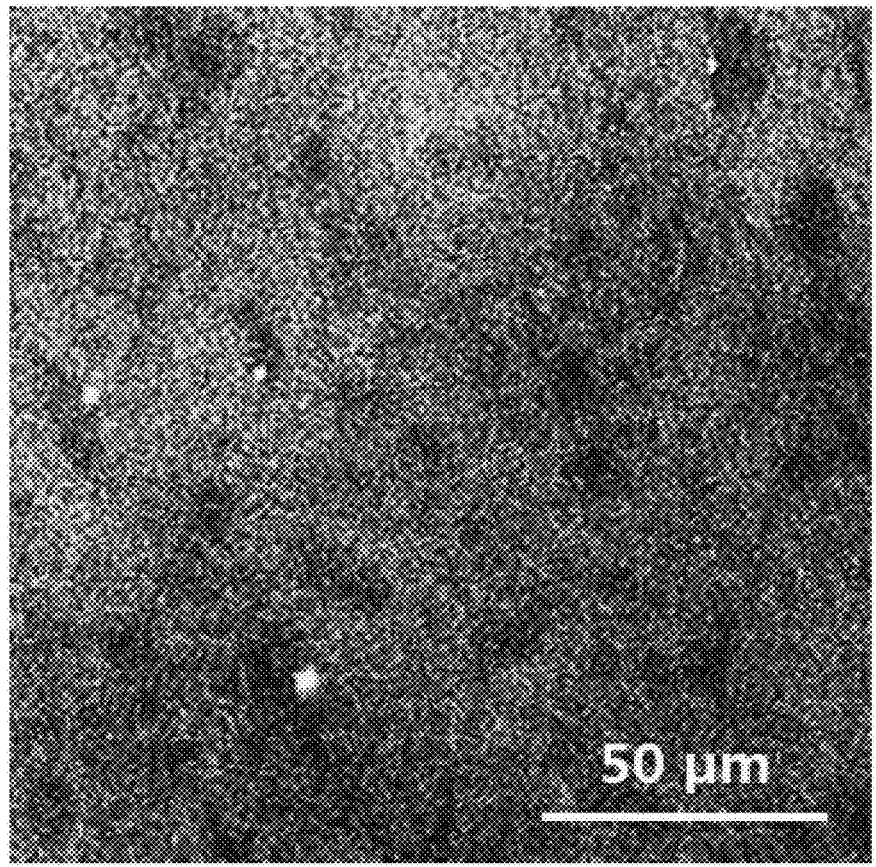
FIGS. 11A, 11B, and 11C illustrate photographs photographing umbrella cells, intermediate cells, and a laminar propria of the bladder lumen tissue which are auto-fluorescently expressed, respectively.
Figure 11B:
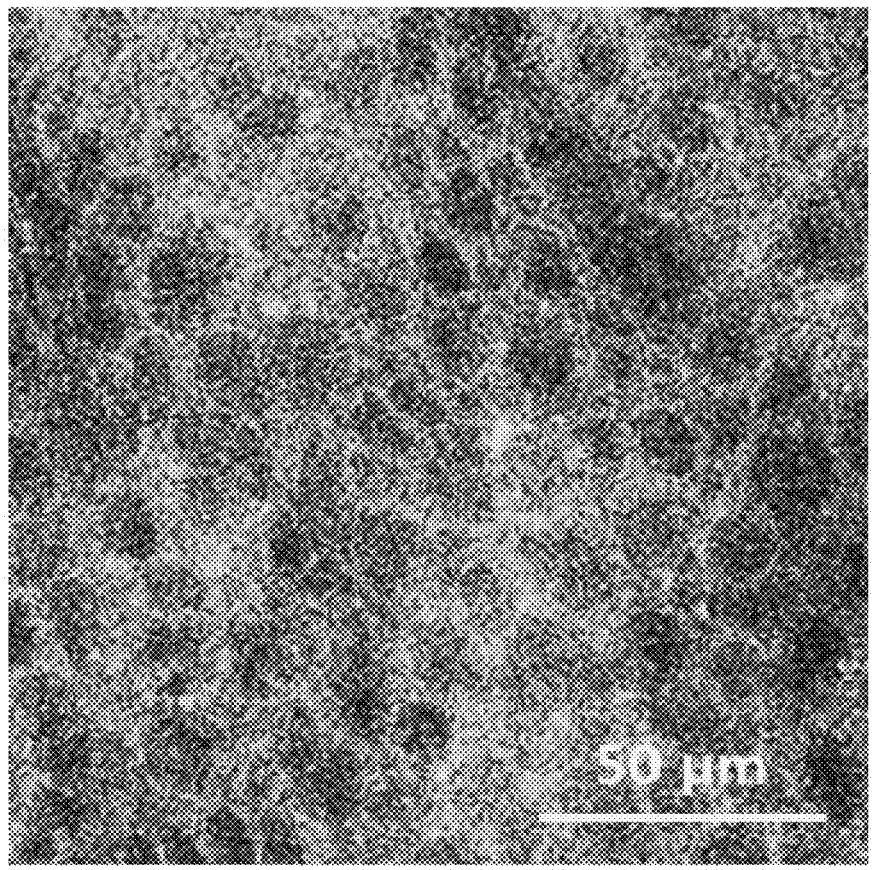
Figure 11C:
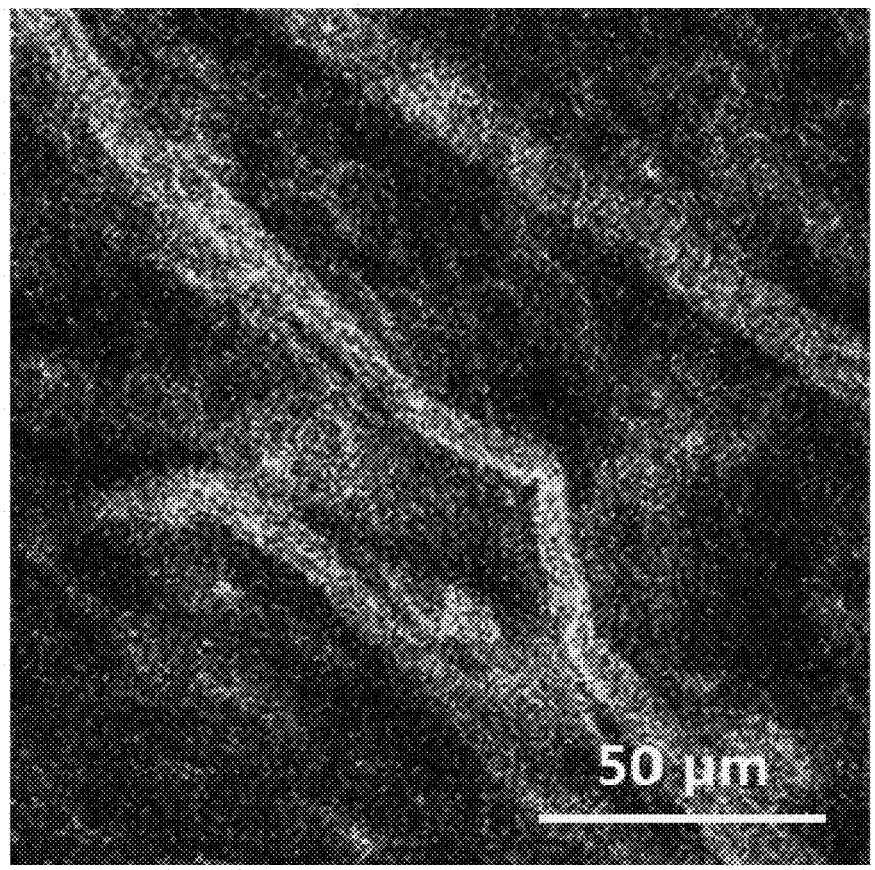
Figure 12A:
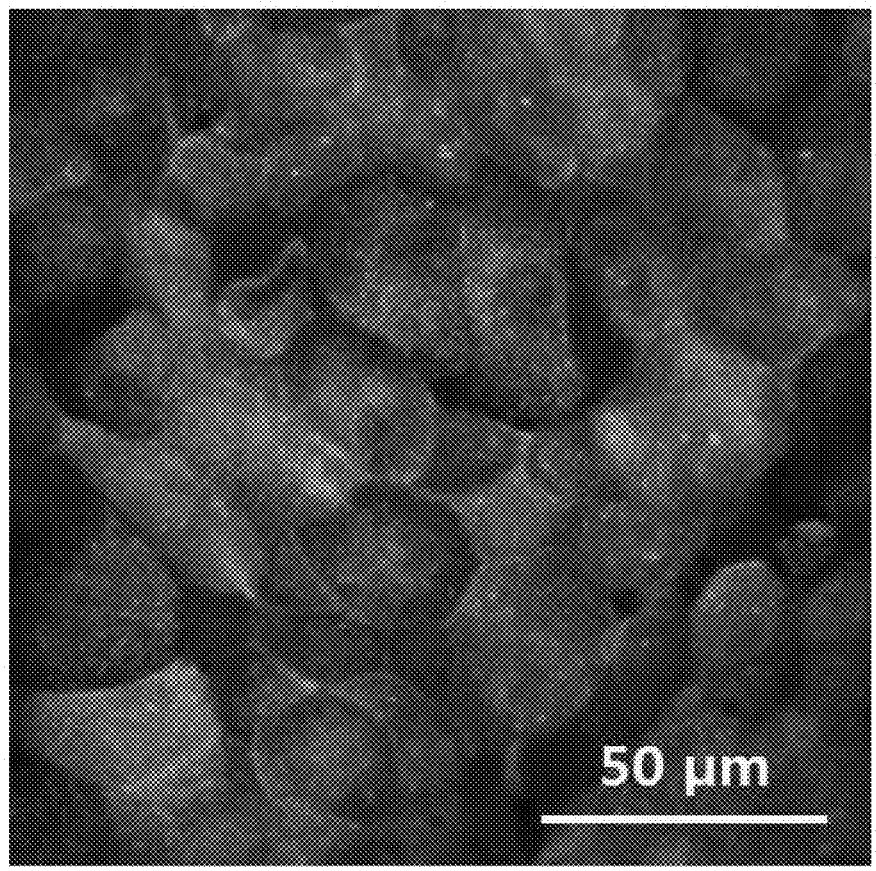
FIGS. 12A, 12B, and 12C are photographs photographing umbrella cells, intermediate cells, and a laminar propria of the bladder lumen tissue which are fluorescently expressed by administering hydrochloride moxifloxacin, respectively.
Figure 12B:
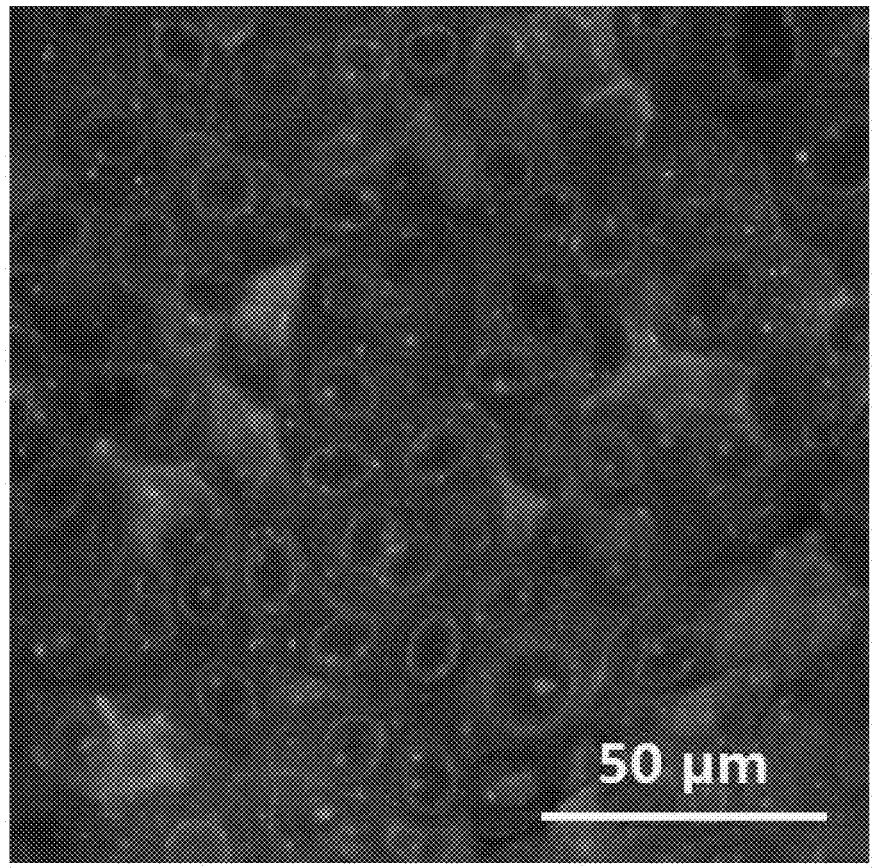
Figure 12C:
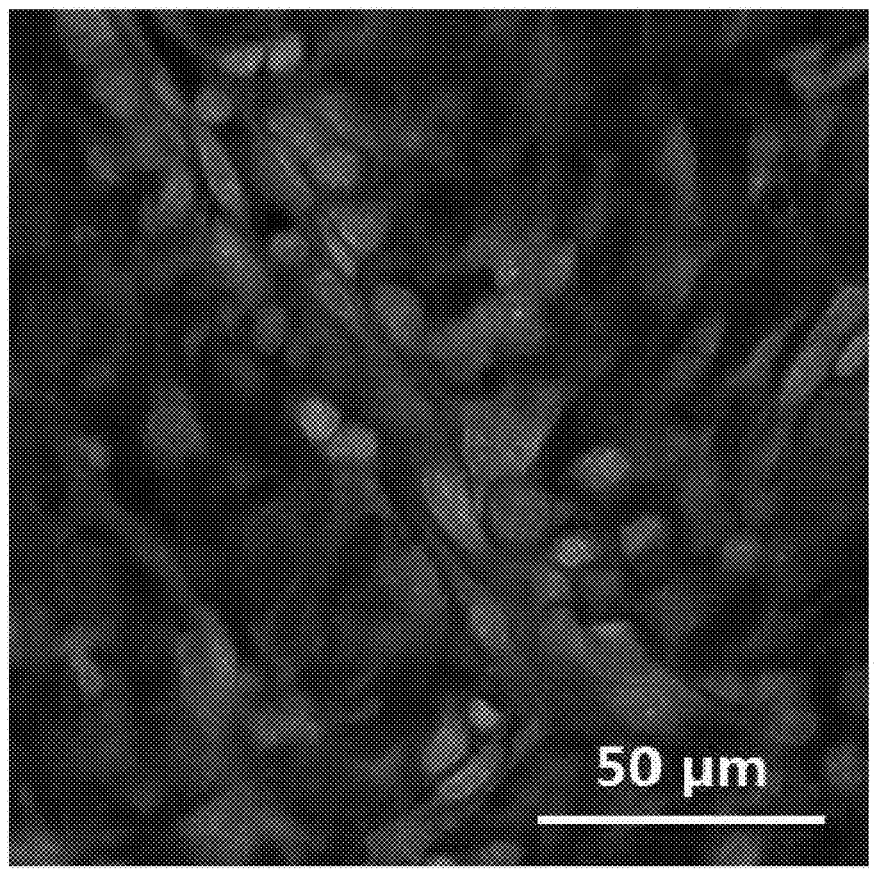

FIGS. 11A to 11C are the lumen of the bladder tissue before administering the hydrochloride moxifloxacin which is photographed by laser power of 300 mW or more while gradually going deep into the inside, and FIGS. 12A to 12C are the lumen of the bladder tissue after administering the hydrochloride moxifloxacin which is photographed by laser power of 15 mW or more while gradually going deep into the inside.

That is, FIGS. 11A and 12A illustrate the umbrella cells, FIGS. 11B and 12B illustrate the intermediate cells, and FIGS. 11C and 12C illustrate the laminar proprias.

When comparing the respective cells, even though the laser power is strong, it was difficult to verify the structure of the cells in the photograph of auto-fluorescence expression before administering the hydrochloride moxifloxacin. Particularly, in the case of the laminar propria, it is difficult to observe the laminar propria because blood vessels are mainly distributed, and after administering the hydrochloride moxifloxacin, even though the intensity of the laser power is decreased to ¹⁄₂₀, the structure of the laminar propria may also be efficiently observed together with peripheral blood vessels.

Figure 13A:
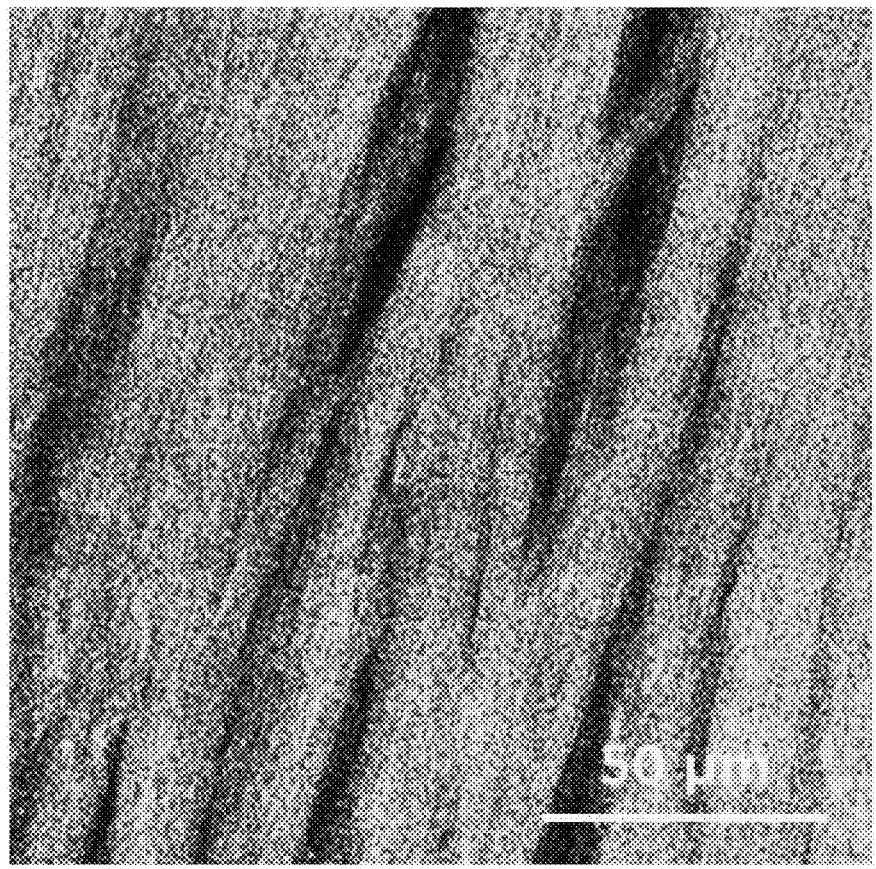
FIGS. 13A, 13B, and 13C illustrate photographs photographing a bladder serosa tissue which is auto-fluorescently expressed while going deep into the inside thereof.
Figure 13B:
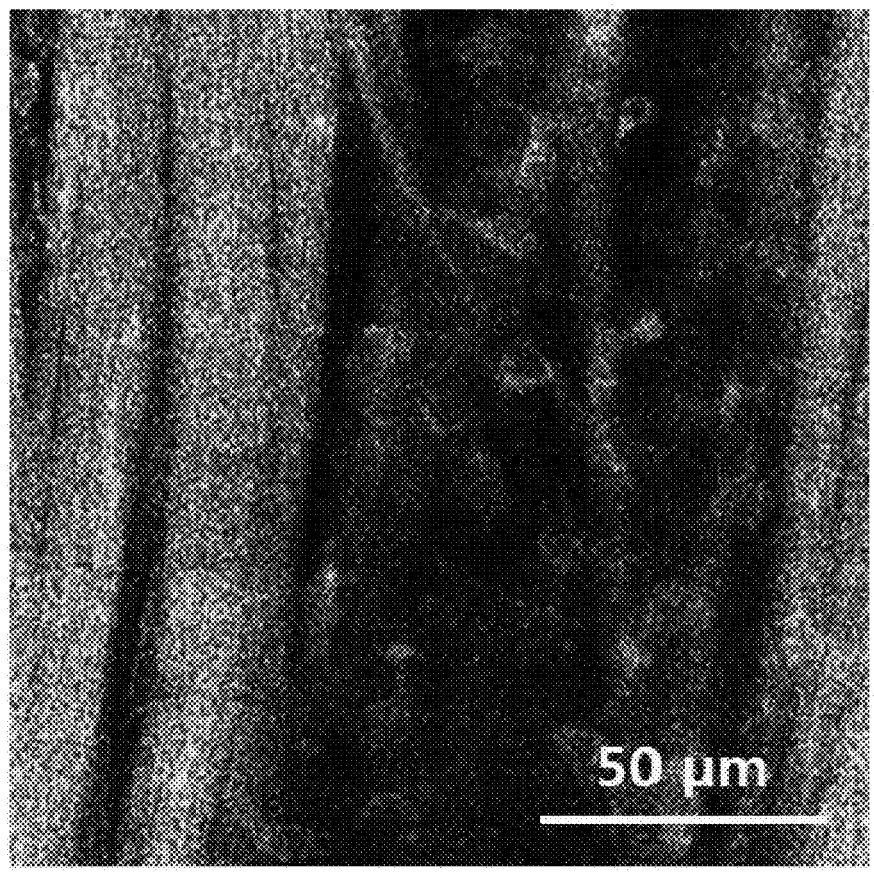
Figure 13C:
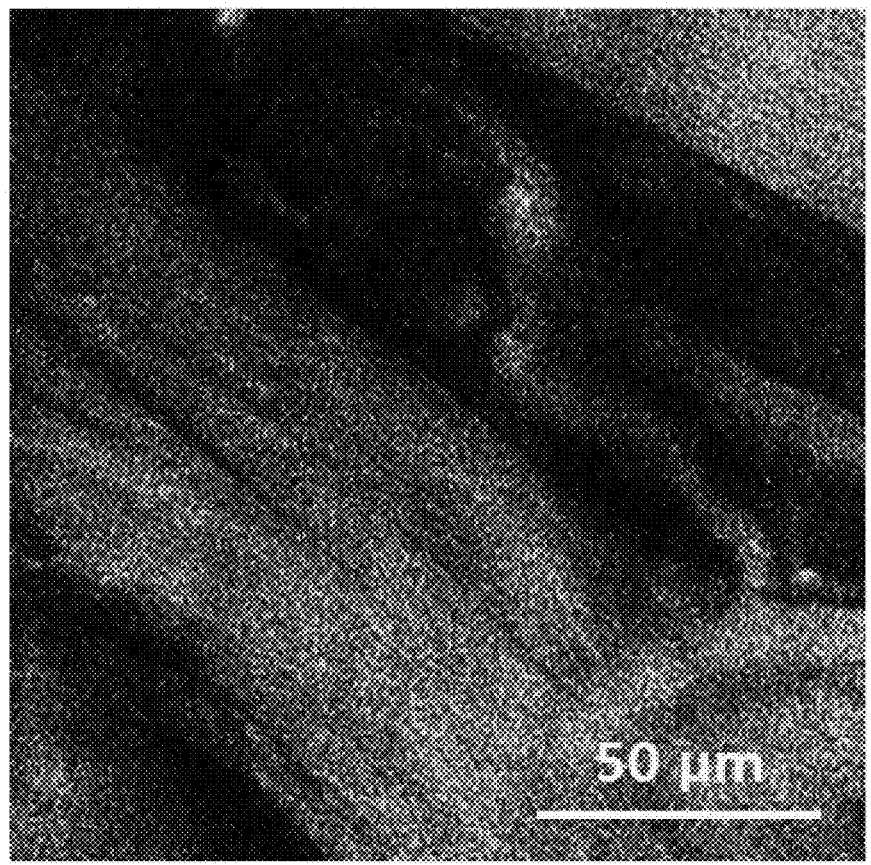
Figure 14A:
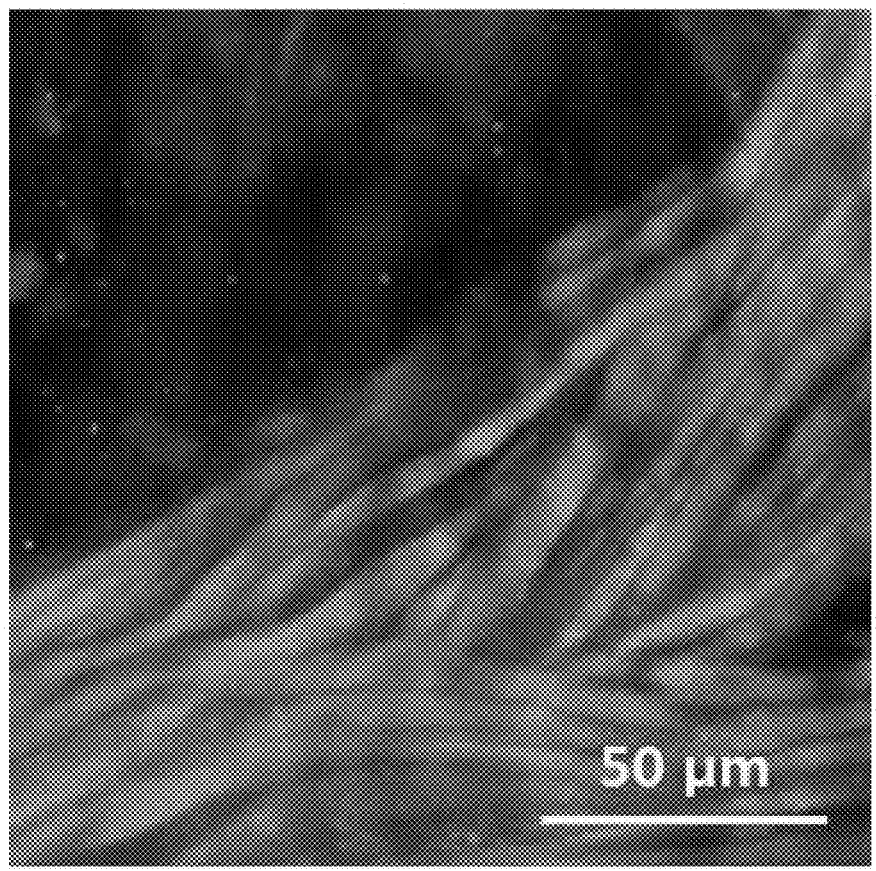
FIGS. 14A, 14B, and 14C illustrate appearances which are fluorescent-expressed by administering hydrochloride moxifloxacin to the bladder serosa tissue at the same position as FIGS. 14A, 14B, and 14C, respectively.
Figure 14B:
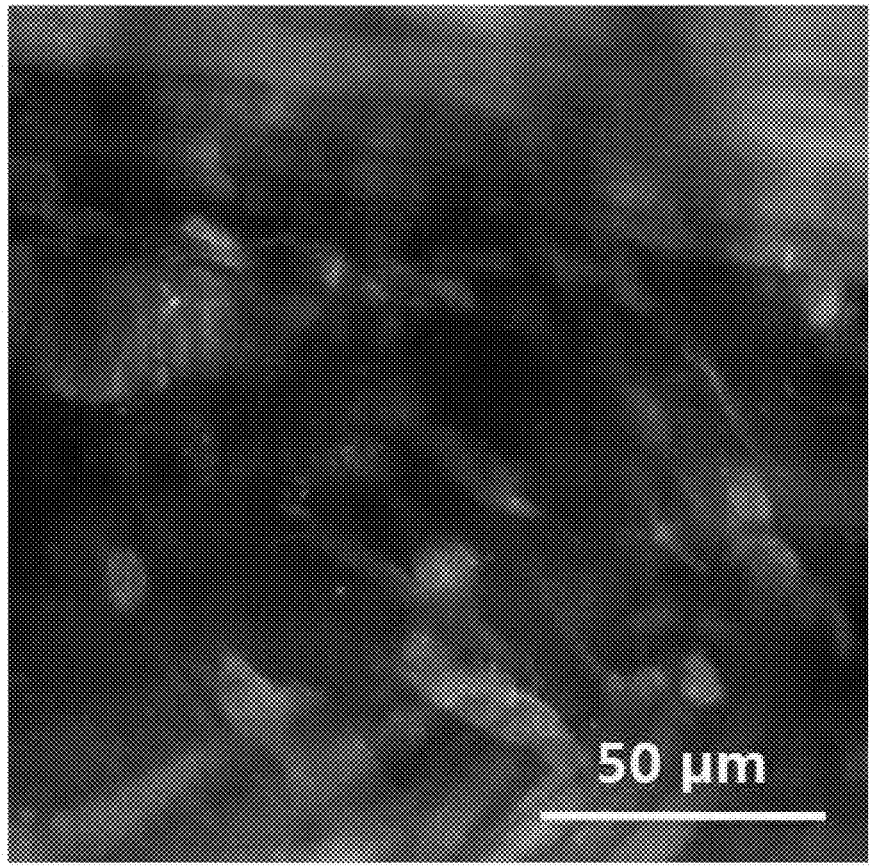
Figure 14C:
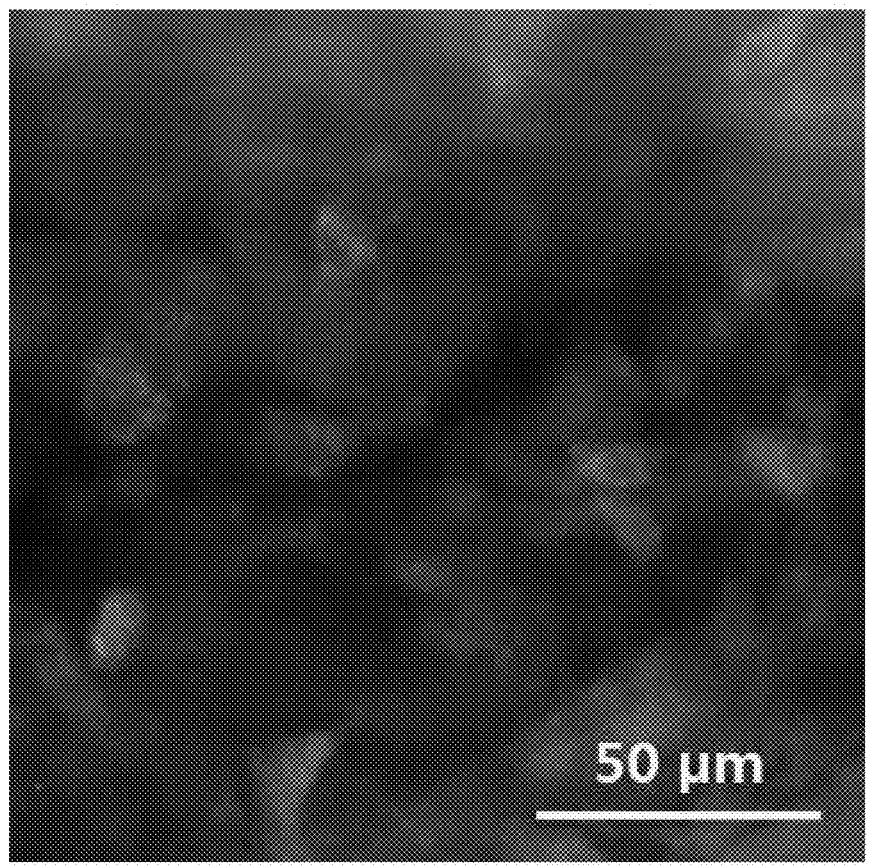

FIGS. 13A to 13C and 14A to 14C illustrate S2 of FIG. 10B as the outside of the bladder cell which is enlarged at 150 μm×150 μm. FIGS. 13A to 13C are the serosa of the bladder tissue before administering the hydrochloride moxifloxacin which is photographed by laser power of 200 mW or more while gradually going deep into the inside, and FIGS. 14A to 14C are the serosa of the bladder tissue after administering the hydrochloride moxifloxacin which is photographed by laser power of 10 mW or more while gradually going deep into the inside.

Referring to FIGS. 13A to 13C, a muscular tissue having a grain-pattern shape may be efficiently observed, but it was difficult to obtain an image of cells existing between muscular coats.

Referring to FIGS. 14A to 14C at the same position, it can be seen that the muscular tissue having the grain-pattern shape was observed well even by small laser power and the cells existing between the muscular coats were also observed.

[Experimental Example 4]: Measurement of Multi-Photon Fluorescence in Bacteria of Hydrochloride Moxifloxacin 1) Preparation of Materials and Samples Bacteria (*pseudomonas* and *staphylococcus*) used in the experiment, hydrochloride moxifloxacin, and a biaxial scanner (a galvano scanner of x axis and a galvano scanner of y axis) to be used by a point scanning method were prepared.

In this Experimental Example, a two-photon microscope using a femtosecond laser as a light source was used, and the multi-photon fluorescence was equally measured under the following condition throughout an experimental process.

Figure 15A:
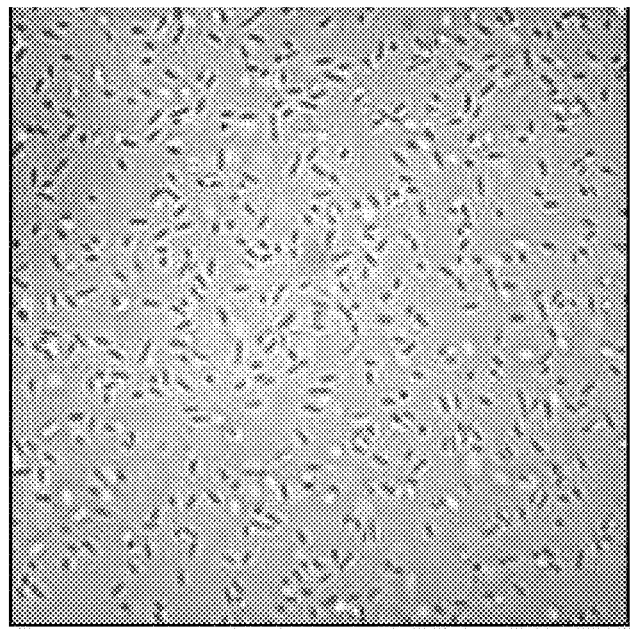
FIGS. 15A and 15B illustrate appearances of *pseudomonas* and *staphylococcus* used in the present experiment which are observed through a microscope, respectively.
Figure 15B:
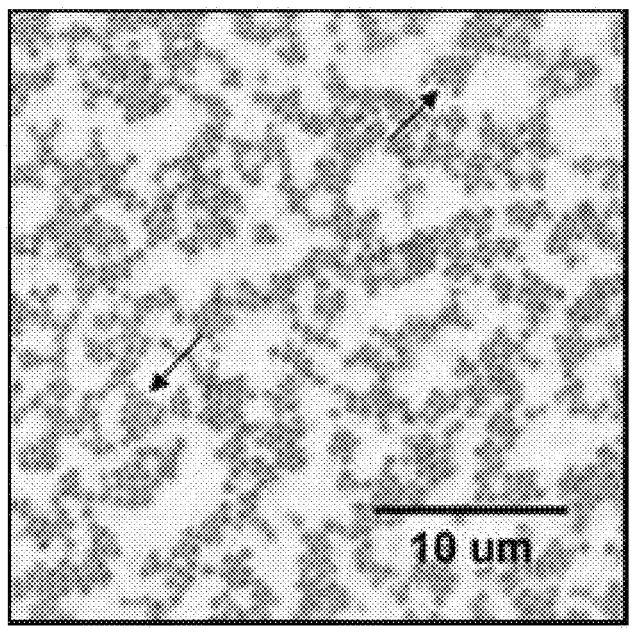

Excitation wavelength: 780 nm for vigamox(moxifloxacin)
  Filter set: Ch01:[430 nm, Ch02:]430 nm
  Manufacturer/Product name of Microscope: Leica/TCS SP5II MP SMD FLIM
  Filter: 500/25 bandpass filter, chroma
  Light source: chameleon vision II, coherent
  Camera: photon multiplier tube (PMT) 6357, Hamamatsu Photonics
  Objective lens: 25×0.95 NA objective lens, leica 2) Measurement of Multi-Photon Fluorescence in Bacteria of Hydrochloride Moxifloxacin FIGS. 15A and 15B illustrate *pseudomonas* and *staphylococcus* as bacteria used in the present experiment, respectively.

The bacteria were incubated under the following condition.

A. Used Medium
  *pseudomonas*-nutrient broth (nutrient medium)
  *staphylococcus*-lysogeny broth (LB medium)

B. Incubation Process

1. A bacteria stock was put in a medium of 3 mL and cultured after overnight incubation (37° C. and 200 rpm).

2. Here, 0.03 mL of the cultured bacteria stock was taken and put in a fresh medium of 3 mL, and then cultured (37° C. and 200 rpm) up to OD600=1.5.

3. The cultured bacteria stock was put in two high-pressure/sterilized e-tubes by 1.0 mL, supernatants thereof were removed by using a centrifugation (6,000×g, 20 min, 4° C.), and then the bacteria stock was resuspended with sterile PBS.

4. In this case, a colony forming unit (CFU) was resuspended by PBS of 0.1 mL and then serial diluted, and the bacteria stock was smeared on an agar plate.

5. Then, the concentration was shown and a PBS volume to be 107 CFU/5 μL may be calculated by the concentration.

C. Experiments of Auto-Fluorescence Expression of Bacteria (Pseudomonas and Staphylococcus) and Fluorescence Expression of Hydrochloride Moxifloxacin In order to compare fluorescence expression of hydrochloride moxifloxacin with auto-fluorescence expression of bacteria, fluorescence expression of bacteria (*pseudomonas* and *staphylococcus*) which are not applied with hydrochloride moxifloxacin was first photographed and intensity of the auto-fluorescence expression was recorded. Subsequently, the hydrochloride moxifloxacin was administered to the medium and then the intensity of the fluorescence expression after the incubation time was measured.

Figure 16A:
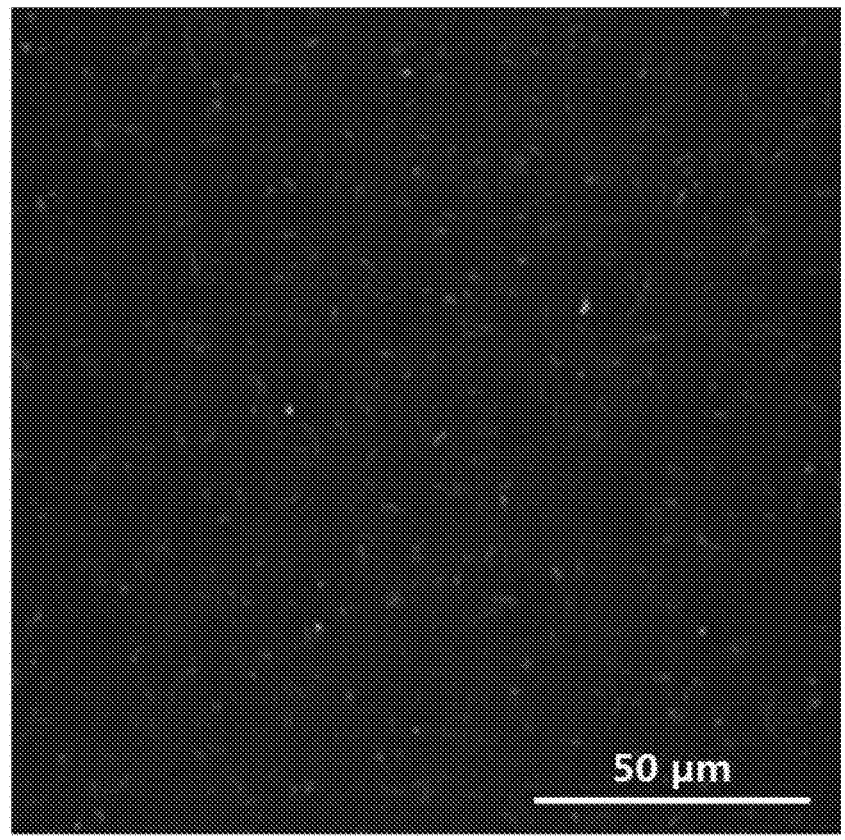
FIGS. 16A to 16B and 17A to 17B illustrate fluorescence expressed photographs of *pseudomonas* before administering hydrochloride moxifloxacin, *pseudomonas* after administering hydrochloride moxifloxacin, *staphylococcus* before administering hydrochloride moxifloxacin, and *staphylococcus* after administering hydrochloride moxifloxacin, respectively.
Figure 16B:
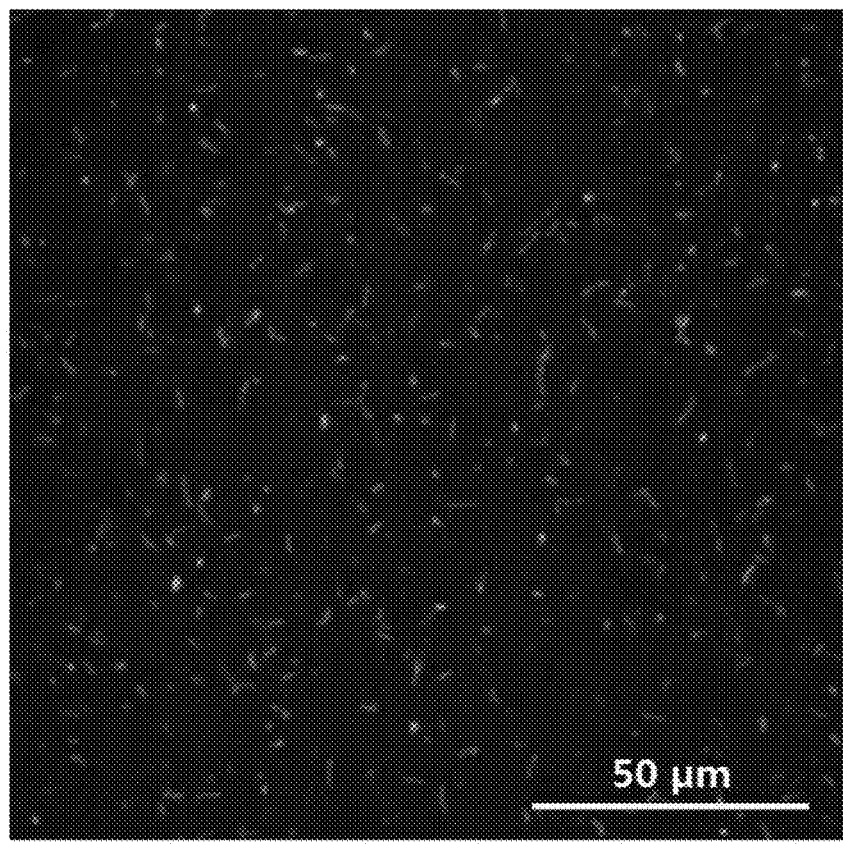
Figure 17A:
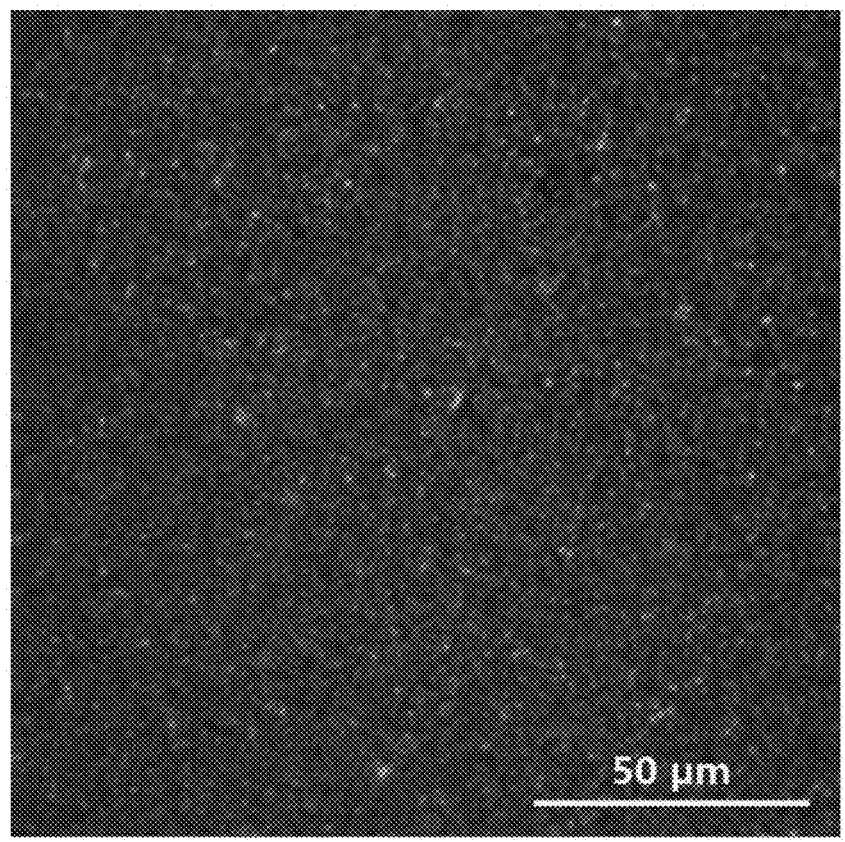
Figure 17B:
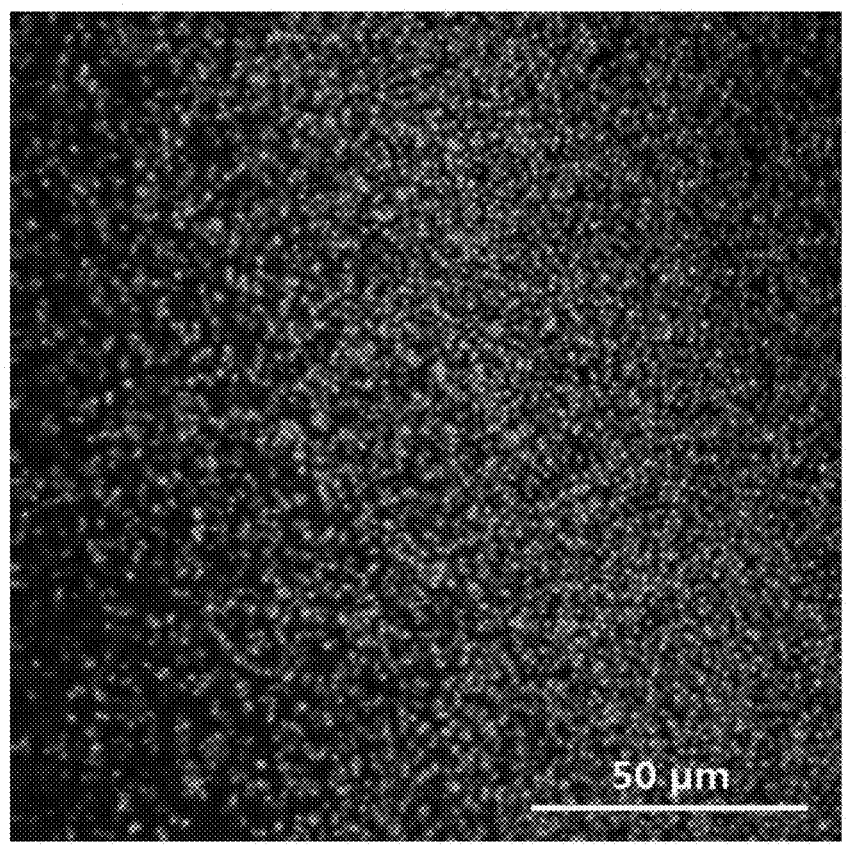

FIGS. 16A and 17A are auto-fluorescence expressed photographs of *pseudomonas* and *staphylococcus* before administering hydrochloride moxifloxacin, respectively, and FIGS. 16B and 17B are fluorescence expressed photographs of *pseudomonas* and *staphylococcus* after administering hydrochloride moxifloxacin, respectively.

First, through FIGS. 16B and 17B, it can be seen that *pseudomonas* and *staphylococcus* may be labeled with the hydrochloride moxifloxacin.

Further, when comparing FIGS. 16A and 16B and FIGS. 17A and 17B, respectively, in the case where the hydrochloride moxifloxacin is administered to each bacterium, a fluorescent signal with a higher intensity than the auto-fluorescence signal may be verified.

Figure 18:
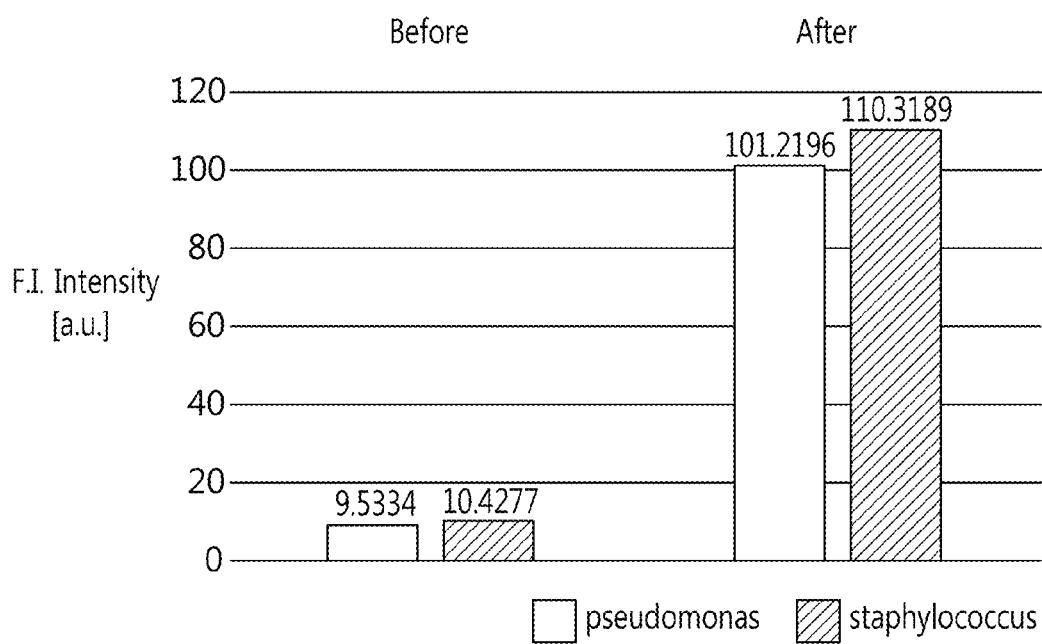
FIG. 18 illustrates a graph before and after administering hydrochloride moxifloxacin to *pseudomonas* and *staphylococcus*.

Values for the accurate fluorescence expression may be verified through a grape illustrated in FIG. 18. In the case of the *pseudomonas*, it can be seen that there is a difference in signal intensity of about 10 times because a value before administering the hydrochloride moxifloxacin is 9.5334 a.u. and a value after administering the hydrochloride moxifloxacin is 101.2196 a.u. Even in the case of the *staphylococcus*, it can be seen that there is a difference in signal intensity of 10 times because a value before administering the hydrochloride moxifloxacin is 10.4277 a.u. and a value after administering the hydrochloride moxifloxacin is 110.3189 a.u.

[Experimental Example 5]: Measurement of Multi-Photon Fluorescence in Fungus of Hydrochloride Moxifloxacin 1) Preparation of Materials and Samples

*Aspergillus* and *candida albican* to be used in the experiment, hydrochloride moxifloxacin, a petri dish, and a biaxial scanner (a galvano scanner of x axis and a galvano scanner of y axis) to be used by a point scanning method were prepared.

In this Experimental Example, a two-photon microscope using a femtosecond laser as a light source was used, and the multi-photon fluorescence was equally measured under the following condition throughout an experimental process.

Excitation wavelength: 790 nm for moxifloxacin
Filter set: Ch01: [490 nm, Ch02:]490 nm
Light source: Chameleon Ultra II, Coherent
Camera: photomultiplier tube (PMT) H7421-40P, Hamamatsu Photonics
Objective lens: 20×LONA objective lens, XLUMPlanFL, Olympus
Photographing area: 150 μm×150 μm (512×512 pixels)

2) Measurement of Multi-Photon Fluorescence in Fungi (*Aspergillus* and *Candida Albican*) of Hydrochloride Moxifloxacin The *aspergillus* and the *candida albican* as the fungi were cultured on the petri dish.

A. Used medium
*aspergillus-niger* agar
*candida*-LB agar

B. Incubation Process

1. First, a nutrient agar was slowly dissolved while being boiled in 1 L of distilled water.
2. An autoclave was performed at 121° C. for about 15 minutes.
3. An agar medium of about 25 to 30 ml was spilled on a plate to prepare a nutrient agar plate.
4. The fungi (*aspergillus* and *candida*) were smeared on the prepared agar plate and incubated at 30° C.
5. A single fungus colony was found after about 24 hours.

C. Sample Preparing Process

1. An appropriate amount of fungi formed on the agar plate with the colony scooped up with a thing such as a toothpick.
2. The toothpick coated with the fungi was put into the e-tube containing distilled water of about 500 ml to be centrifuged (10 min, 4000×g, 4° C.).
3. After the centrifuge, the toothpick was removed and distilled water was mixed with the fungi sunken in the e-tube by using a pipet. About 50 μl of the fungi and the distilled water in the e-tube was extracted and placed on a well-slide glass to prepare a control sample.
4. About 20 μl of a moxifloxacin solution (a vigamox solution) was dropped into the fungi and the distilled water remaining in the e-tube and then centrifuged (10 min, 4000×g, and 4° C.).
5. Thereafter, the remaining solution except for the fungi sunken in the e-tube was removed by using the pipet, distilled water of about 500 ml was added, and then mixed by using the pipet.
6. About 50 μl of a mixed solution of the fungi and the distilled water in the e-tube was extracted to be placed on the well-slide glass to prepare a moxifloxacin (vigamox) labelled fungus sample.

D. Experiment of Auto-Fluorescence Expression of Fungi (*Aspergillus* and *Candida Albican*) and Fluorescence Expression of Hydrochloride Moxifloxacin In order to compare auto-fluorescence expression of fungi (*aspergillus* and *candida albican*) and fluorescence expression of hydrochloride moxifloxacin, first, fluorescence expression of fungi (*aspergillus* and *candida albican*) which are not applied with the hydrochloride moxifloxacin was photographed and then intensity of the fluorescence expression was recorded.

Subsequently, after the hydrochloride moxifloxacin was administered to the petri dish and sufficiently smeared for 10 minutes, the fungi (*aspergillus* and *candida albican*) were collected by using a centrifuge and the intensity of the fluorescence expression was measured.

An experimental result will be described in detail with reference to FIGS. 19A to 19C and 20A to 20C.

Figure 19A:
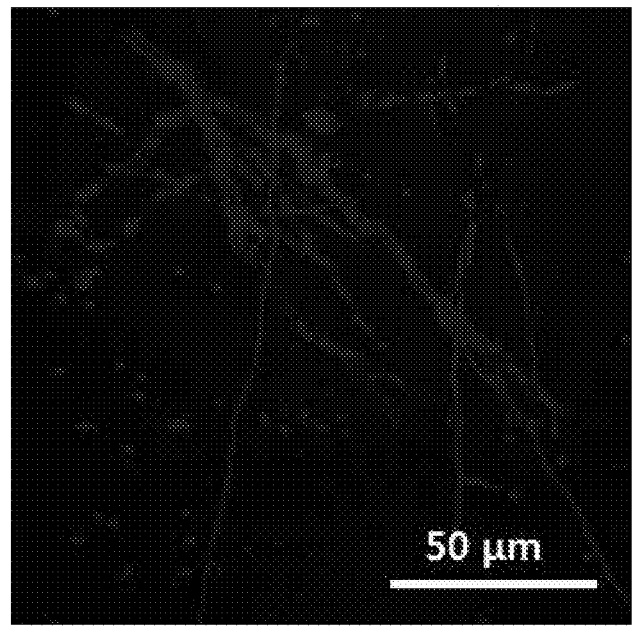
FIGS. 19A and 20A are auto-fluorescent expressed photographs of *aspergillus* and *candida albican* before administering hydrochloride moxifloxacin which are photographed by laser power of 7 mW, respectively.
Figure 19B:
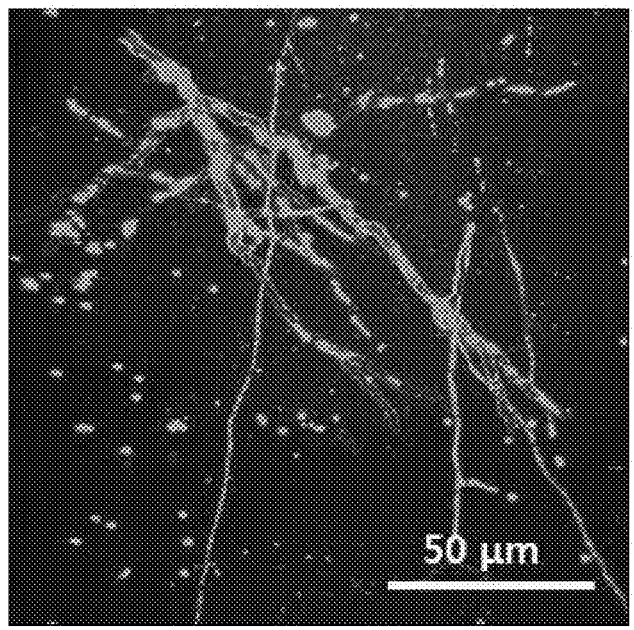
FIGS. 19B and 20B are auto-fluorescent expressed photographs of *aspergillus* and *candida albican* which are photographed by laser power of 50 mW, respectively.
Figure 20A:
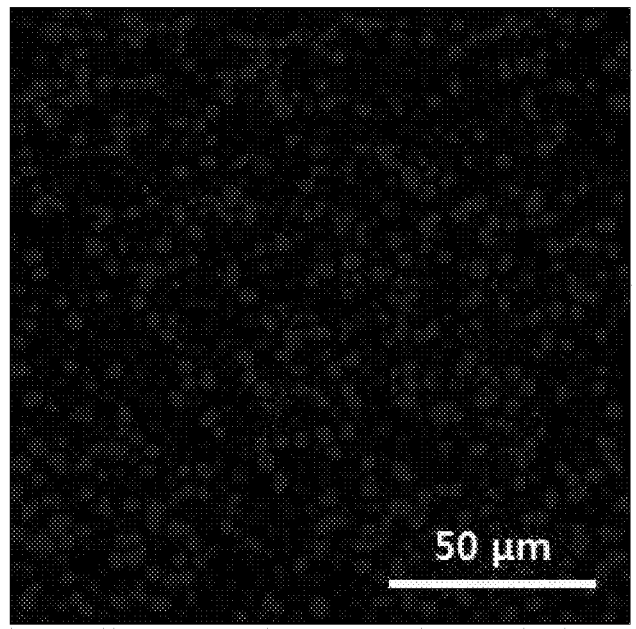
Figure 20B:
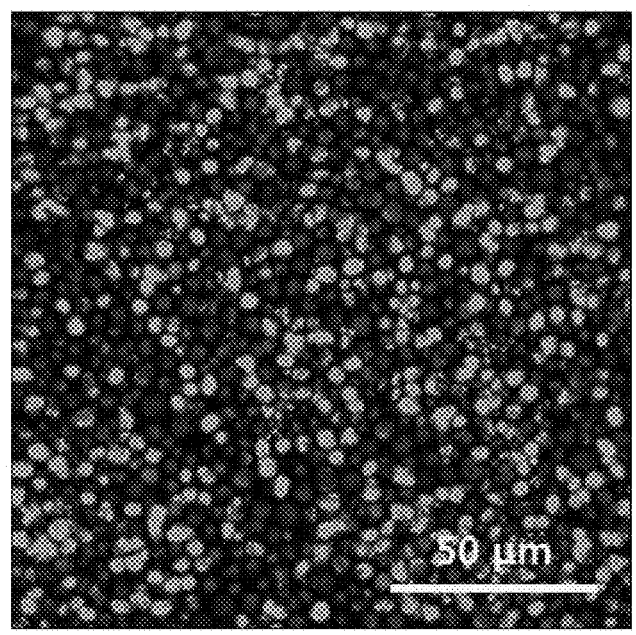

FIGS. 19A and 20A are auto-fluorescence expression photographs of *aspergillus* and *candida albican* before administering hydrochloride moxifloxacin which are photographed by laser power of 7 mW, respectively, and FIGS. 19B and 20B are auto-fluorescence expression photographs of *aspergillus* and *candida albican* which are photographed by laser power of 50 mW, respectively.

First, referring to FIGS. 19A and 20A, it can be seen that a structure of the fungi was verified with the laser power of 7 mW. Further, as illustrated in FIGS. 19B and 20B, structures of *aspergillus* having an elongated branch shape and *candida albican* having a spherical particle shape may be verified in the laser power of about 50 mW.

Figure 19C:
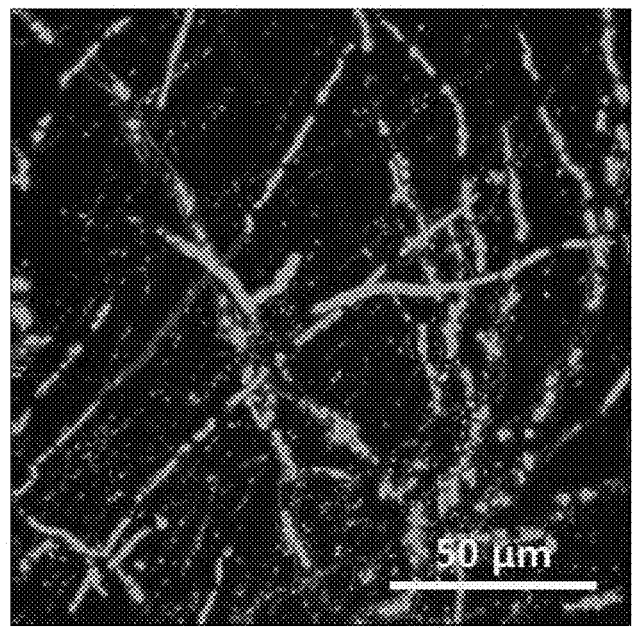
FIGS. 19C and 20C are photographs of *aspergillus* and *candida albican* after administering hydrochloride moxifloxacin which are photographed by laser power of 7 mW, respectively
Figure 20C:
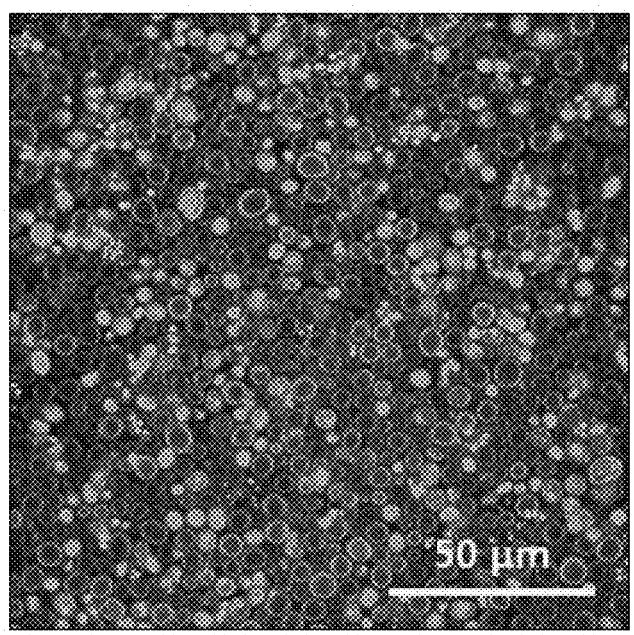

FIGS. 19C and 20C are photographs of *aspergillus* and *candida albican* after administering hydrochloride moxifloxacin which are photographed by laser power of 7 mW, respectively. In comparison with FIGS. 19A and 20A, respectively, it can be seen that the structures of *aspergillus* and *candida albican* may be efficiently verified even with the laser power of 7 mW.

Further, in the *aspergillus* of FIG. 19C, the structure of the *aspergillus* may be more clearly observed by using the laser power with small intensity while minimizing a signal corresponding to background noise. Even in the *candida albican* of FIG. 20C, an empty nucleus existing in the bacteria may be more clearly observed with smaller laser power than that of FIGS. 20A and 20B.

That is, the fluoroquinolone antibiotics may label the bacteria and the fungi, and in this case, the intensity of the fluorescence expression is 10 times stronger than the auto-fluorescence. As illustrated in Experimental Examples 1 to 3, since the cell tissue in the body tissue may be labeled, it can be seen that whether the bacteria exist in the body may be easily determined only by administration of the antibiotic.

The fluoroquinolone antibiotics may be easily obtained as antibiotics which are sold to be clinically used and have an advantage of observing the cells while minimizing the damage. In this case, the tissue to be observed may be high-speed imaged in vivo without extraction of the tissue or incubation of the cell.

Further, even in addition to the cornea, the skin and bladder cells may be labeled, and as a result, the fluoroquinolone antibiotics may be used as an inspection method of cell fluorescent chromosomes and cells of various biological tissues.

Since the fluoroquinolone antibiotics may express the fluorescent signal of a minimum of 10 times more than the auto-fluorescent signal in the cells, even though the laser power having a small value is used, the cells in the body tissue may be observed. Particularly, in addition to labeling of the vascular endothelia cells and fluorescent labeling of the bacteria, the fungi consisting of a eukaryote such as a human may be labeled, and as a result, the fluoroquinolone antibiotics may be used for inspection of the infectious bacteria of various tissues and cells.

Particularly, a time may be more shortened than the existing diagnosis method of the infectious bacteria in which cells are extracted and cultured for several days, and as a result, there is an advantage of advancing a treatment time.

The above Experimental Examples are just examples for describing the present invention, and the present invention is not limited thereto. Since those skilled in the art can implement the present invention through various modifications therefrom, the technical protection scope should be determined by the appended claims.

What is claimed is:

1. A method of labeling cells, the method comprising:
   (a) preparing a biological tissue, bacterial cell, or fungal cell;
   (b) adding, to the prepared biological tissue, bacterial cell, or fungal cell; a fluoroquinolone antibiotic; and
   (c) examining cells within the biological tissue, bacterial cell, or fungal cell with multi-photon fluorescence microscopy.

2. The method of claim 1, wherein the tissue includes at least one of a cornea, a skin, and a bladder.

3. The method of claim 1, wherein the fluoroquinolone antibiotics include moxifloxacin.

4. The method of claim 1, wherein the fluoroquinolone antibiotics include gatifloxacin.

* * * * *